United States Patent
Cherubini et al.

(10) Patent No.: US 12,253,535 B2
(45) Date of Patent: Mar. 18, 2025

(54) MODULE FOR AN AUTOMATED LABORATORY SYSTEM

(71) Applicant: Roche Diagnostics Operations, Inc., Indianapolis, IN (US)

(72) Inventors: Claudio Cherubini, Cham (CH); Andreas Drechsler, Baar (CH); Reto Huesser, Hagendorn (CH); Ivan Heinzer, Brunnen (CH)

(73) Assignee: ROCHE DIAGNOSTICS OPERATIONS, INC., Indianapolis, IN (US)

(*) Notice: Subject to any disclaimer, the term of this patent is extended or adjusted under 35 U.S.C. 154(b) by 780 days.

(21) Appl. No.: 17/328,214

(22) Filed: May 24, 2021

(65) Prior Publication Data

US 2021/0373042 A1 Dec. 2, 2021

(30) Foreign Application Priority Data

May 29, 2020 (EP) ..................................... 20177378

(51) Int. Cl.
*G01N 35/04* (2006.01)
*B01L 9/02* (2006.01)
(Continued)

(52) U.S. Cl.
CPC .............. *G01N 35/04* (2013.01); *B01L 9/02* (2013.01); *G05D 3/20* (2013.01); *G06T 1/0014* (2013.01);
(Continued)

(58) Field of Classification Search
CPC ......... B01L 2200/025; B01L 2200/028; B01L 2200/18; B01L 2300/021; B01L 9/02;
(Continued)

(56) References Cited

U.S. PATENT DOCUMENTS

| | | | |
|---|---|---|---|
| 5,510,833 A | * 4/1996 | Webb | H04N 17/04 348/E17.005 |
| 5,651,941 A | 7/1997 | Stark et al. | |

(Continued)

FOREIGN PATENT DOCUMENTS

| | | |
|---|---|---|
| CN | 1533496 | 9/2004 |
| CN | 110520738 | 11/2019 |

(Continued)

OTHER PUBLICATIONS

JP 6670974B1 published Mar. 2020, english translation (Year: 2023).*

(Continued)

*Primary Examiner* — Jennifer Wecker
*Assistant Examiner* — Jonathan Bortoli
(74) *Attorney, Agent, or Firm* — Woodard, Emhardt, Henry, Reeves & Wagner, LLP

(57) ABSTRACT

A module for an automated laboratory system is disclosed. The module comprises a module connector configured to releasably connect to a component of the automated laboratory system, a detector at least configured to detect at least one component marker located at the component so as to obtain position data of the module indicating an actual position of the module, a processor configured to calculate a position deviation of the module from a target position defined by the component based on the position data and to calculate position alignment data based on the position deviation, and a alignment device configured to align the module to the target position based on the position alignment data. Further, an automated laboratory system and a method for aligning a module are disclosed.

18 Claims, 10 Drawing Sheets

(51) Int. Cl.
  *G05D 3/20* (2006.01)
  *G06T 1/00* (2006.01)
  *G06T 7/30* (2017.01)
  *G06T 7/70* (2017.01)
  *G16H 10/40* (2018.01)

(52) U.S. Cl.
  CPC .................. *G06T 7/30* (2017.01); *G06T 7/70* (2017.01); *G16H 10/40* (2018.01); *B01L 2200/025* (2013.01); *B01L 2200/028* (2013.01); *B01L 2200/18* (2013.01); *B01L 2300/021* (2013.01); *G01N 2035/0465* (2013.01); *G06T 2207/30204* (2013.01)

(58) Field of Classification Search
  CPC . G01N 2035/00326; G01N 2035/0465; G01N 35/00; G01N 35/02; G01N 35/04; G05D 3/20; G06T 1/0014; G06T 2207/30204; G06T 7/30; G06T 7/70; G16H 10/40
  See application file for complete search history.

(56) References Cited

U.S. PATENT DOCUMENTS

| | | | |
|---|---|---|---|
| 2006/0022976 A1 | 2/2006 | Bredow et al. | |
| 2006/0083660 A1 | 4/2006 | Schorno et al. | |
| 2006/0229763 A1* | 10/2006 | Haas | G01N 35/0099 700/220 |
| 2007/0237675 A1 | 10/2007 | Nichols et al. | |
| 2008/0228319 A1* | 9/2008 | Ding | G01N 35/0099 901/9 |
| 2011/0205108 A1* | 8/2011 | Boyer | G01S 5/06 342/451 |
| 2012/0270305 A1* | 10/2012 | Reed | G01N 21/05 422/560 |
| 2013/0259635 A1* | 10/2013 | Maslana | G01N 35/0099 422/501 |
| 2014/0262619 A1* | 9/2014 | Bains | E04G 7/34 248/351 |
| 2015/0243473 A1* | 8/2015 | Price | H01J 37/023 250/442.11 |
| 2015/0355208 A1* | 12/2015 | German | G01N 35/021 422/65 |
| 2019/0096083 A1* | 3/2019 | Arano | G06T 7/70 |
| 2019/0263596 A1* | 8/2019 | DeGroot | B65G 21/06 |
| 2019/0344260 A1* | 11/2019 | Ergezen | B01L 9/52 |

FOREIGN PATENT DOCUMENTS

| | | | | |
|---|---|---|---|---|
| EP | 2902790 A1 | 8/2015 | | |
| EP | 2907576 A1 | 8/2015 | | |
| JP | 6670974 B1 * | 3/2020 | ............ | B25J 19/021 |
| KR | 10-2018-0129242 A | 12/2018 | | |
| KR | 10-2000825 B1 | 7/2019 | | |
| WO | WO 2013/070756 | 5/2013 | | |
| WO | 2016/012517 A1 | 1/2016 | | |
| WO | 2016/133919 A1 | 8/2016 | | |

OTHER PUBLICATIONS

European Search Report issued Oct. 14, 2020, in Application No. 20177378.5, 2 pp.

Hildebrandt, Marc et al., Combining Cameras, Magnetometers and Machine-Learning into a Close Range Localization System for Docking Homing, Underwater Robotics Department DFKI RIC Bremen, 2017, 6 pp.

Popescu, Dragos C. et al., An assessment on the accuracy of high precision 3D positioning using planar fiducial markers, 21st International Conference on System Theory, Control and Computing (ICSTCC), 2017, pp. 471-476, Bucharest, Romania.

* cited by examiner

MODULE FOR AN AUTOMATED LABORATORY SYSTEM

CROSS-REFERENCE TO RELATED APPLICATIONS

This application claims priority to European Patent Application No. 20177378.5, filed 29 May 2020, the disclosure of which is hereby incorporated by reference in its entirety.

TECHNICAL FIELD

The disclosure relates to a module for an automated laboratory system, to an automated laboratory system, and to a method for aligning a module.

BACKGROUND

Laborsaving for examination work in the medical field has recently proceeded by introducing diverse automated devices. For example, for testing in a hospital, the samples of inpatients and out-patients are collected from several sections of the hospital and collectively processed in an examination room. Test items for each sample are sent from doctors to the examination room by use of an online information processing system. Test results are then reported online from the examination room to the doctors. For many of test items on blood or urine, pretreatment for testing needs to be performed such as centrifugal process, unplugging, dispensing, and the like. It takes much time for engagement in such pretreatment work in total testing working hours.

Next, the flow of a process to be performed by a general automated sample testing system is described. A vessel such as test tube that holds a body fluid such as blood collected from a patient is held by a vessel carrier. Such vessel carriers are known and described, e.g., in EP 2 907 576, WO 2016/012517 or U.S. Pat. No. 5,651,941. The vessel carrier holding the vessel such as the test tube is loaded into the general automated sample testing system. Barcode information of the loaded sample is read in the system so that the sample type is recognized. As described above, the centrifugal process, unplugging, dispensing, and the like are performed as the pretreatment for the test process.

The contents of the pretreatment vary depending on the sample type, for example, for a urine test or a hematological sample, the centrifugal process does not necessarily need to be performed. A sample type that needs to be subjected to the centrifugal separation is a sample on which the unplugging and dispensing are performed after centrifugal separation. However, samples could also arrive which are already centrifuged with no centrifugation within the system is needed but the other pretreatment steps. The dispensing process usually known as aliquoting is a process in which a child sample is generated from a parent sample. For example, dispensed child samples can be simultaneously transported to multiple analyzers that are connected to the system online. A sample that is completed with all processes is stored in a storage module.

The automated sample testing system is introduced in a relatively large facility where hundreds to thousands samples are processed in a day or even per hour. In such large facility, many samples are collected from one patient for multiple testing such as a biochemical test, an immunological test, a solidification test, and a hematological test. Therefore, the number of sample carriers for the hundreds to thousands patients are needed for loading into the automated sample testing system, and accordingly, a space for installing such a sample testing system is required.

Modern automated integrated laboratory solutions usually have a transport system for sample tubes as a backbone. The sample tubes can be transported using single tube carrier or racks. Individual modular system components, which are also called modules hereinafter, with pre-/post-analytical or analytical functionality are attached to the transportation backbone. The positions are precisely defined corresponding to a defined grid, but should be flexible to be re-arranged or be reconfigurable as desired. Such modular system components, which are also called modules hereinafter, are well known such as from US 2006/229763 A1.

The installation of such a module should be done in a reasonable time. For service and maintenance, it might be necessary to temporarily disconnect and remove modules from the transport system. This is the case if parts within the module or of the transport system are neither accessible from the front nor from the back since reach is outside the permitted range. This is particularly the case if the depth of the modules or the width of the transport system exceed the permitted ranges. The disconnection could also be required if modular system components have to be removed to be replaced. The removal of modules should ideally be feasible without removing neighbour components.

Replacement and positioning of modules relative to the transport system is very complex and must be done with high precision. At present, this is a very time-consuming process or not practical, if additional parts of the system must be removed. Although purely mechanical solutions enable pre- or course positioning with high reproducibility, these methods cannot offer very high precision without manual alignment and cannot react on changes in the system, e.g., due to mechanical or thermal drift over time or ground movements (shifts within floor level due to settling, etc.).

SUMMARY

Although the embodiments of the present disclosure are not limited to specific advantages or functionality, it is noted that in accordance with the present disclosure the disclosed module and automated laboratory system aim to provide a standardized interface to align a modular system component or module with high precision and accuracy to a transport system or another modular system component or module.

In accordance with one embodiment of the present disclosure, a module for an automated laboratory system is provided comprising a module connector configured to releasably connect to a component of the automated laboratory system, a detector at least configured to detect at least one component marker located at the component so as to obtain position data of the module indicating an actual position of the module, a processor configured to calculate a position deviation of the module from a target position defined by the component based on the position data and to calculate position alignment data based on the position deviation, and an alignment device configured to align the module to the target position based on the position alignment data.

In accordance with another embodiment of the present disclosure, a method for aligning a module according to an embodiment of the present disclosure is provided comprising releasably connecting the module to a component of the automated laboratory system, wherein releasably connecting the module to the component of the automated laboratory system provides a rough aligning of the module relative to the component, detecting at least one component marker located at the component so as to obtain position data of the module indicating an actual position of the module, calculating a position deviation of the module from a target position defined by the component based on the position data and position alignment data based on the position deviation, and aligning the module to the target position based on the position alignment data.

These and other features and advantages of the embodiments of the present disclosure will be more fully understood from the following detailed description taken together with the accompanying claims. It is noted that the scope of the claims is defined by the recitations therein and not by the specific discussions of features and advantages set forth in the present description.

BRIEF DESCRIPTION OF THE DRAWINGS

The following detailed description of the embodiments of the present description can be best understood when read in conjunction with the following drawings, where like structure is indicated with like reference numerals and in which.

Figure 1:
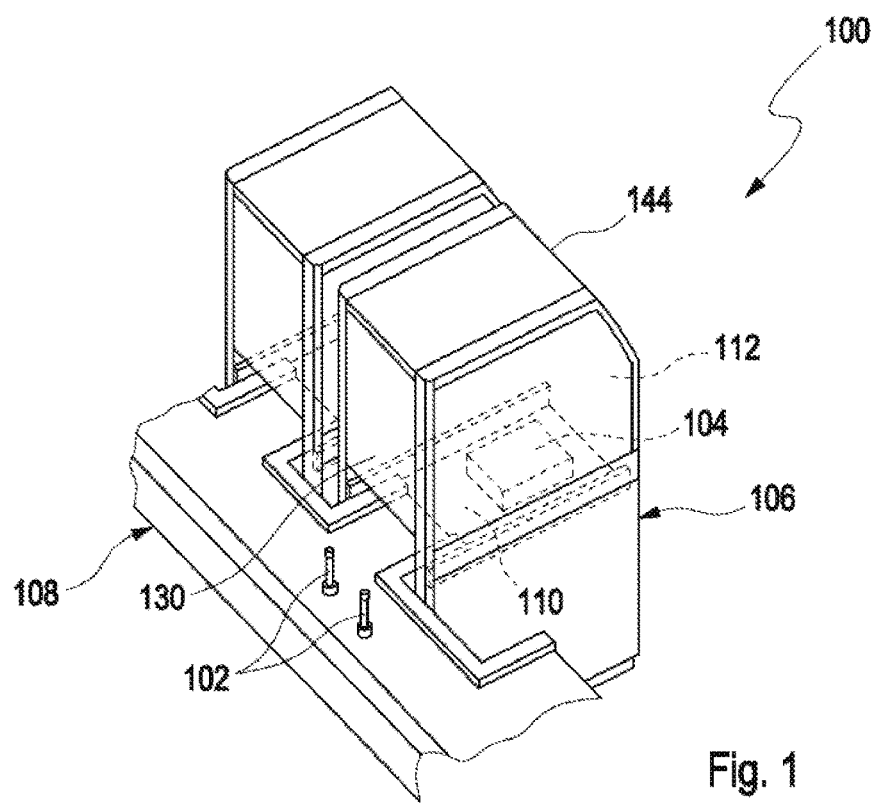
FIG. 1 shows a perspective view of an automated laboratory system.

Skilled artisans appreciate that elements in the figures are illustrated for simplicity and clarity and have not necessarily been drawn to scale. For example, dimensions of some of the elements in the figures may be exaggerated relative to other elements to help improve understanding of the embodiment(s) of the present disclosure.

DETAILED DESCRIPTION

As used in the following, the terms "have", "comprise" or "include" or any arbitrary grammatical variations thereof are used in a non-exclusive way. Thus, these terms may both refer to a situation in which, besides the feature introduced by these terms, no further features are present in the entity described in this context and to a situation in which one or more further features are present. As an example, the expressions "A has B", "A comprises B" and "A includes B" may both refer to a situation in which, besides B, no other element is present in A (i.e., a situation in which A solely and exclusively consists of B) and to a situation in which, besides B, one or more further elements are present in entity A, such as element C, elements C and D or even further elements.

Further, it shall be noted that the terms "at least one", "one or more" or similar expressions indicating that a feature or element may be present once or more than once typically will be used only once when introducing the respective feature or element. In the following, in most cases, when referring to the respective feature or element, the expressions "at least one" or "one or more" will not be repeated, non-withstanding the fact that the respective feature or element may be present once or more than once.

Further, as used in the following, the terms "preferably", "more preferably", "particularly", "more particularly", "specifically", "more specifically", "typically", "more typically", or similar terms are used in conjunction with optional features, without restricting alternative possibilities. Thus, features introduced by these terms are optional features and are not intended to restrict the scope of the claims in any way. The disclosure may, as the skilled person will recognize, be performed by using alternative features. Similarly, features introduced by "in an embodiment of the disclosure" or similar expressions are intended to be optional features, without any restriction regarding alternative embodiments of the disclosure, without any restrictions regarding the scope of the disclosure and without any restriction regarding the possibility of combining the features introduced in such way with other optional or non-optional features of the disclosure.

According to one embodiment of the present disclosure a module for an automated laboratory system is provided. The module comprises a module connector configured to releasably connect to a component of the automated laboratory system. The module further comprises a detector at least configured to detect at least one component marker located at the component so as to obtain position data of the module indicating an actual position of the module. The module further comprises a processor configured to calculate a position deviation of the module from a target position defined by the component based on the position data and to calculate position alignment data based on the position deviation. The module further comprises an alignment device configured to align the module to the target position based on the position alignment data.

Thus, the module may be detachably connected to a component such as another module or a transport line of the automated laboratory system by means of the module connector. The module connector prevents an unintended separation of the module from the component. The detector allows to determine the position of the module relative of the component to which it is intended to be connected. Thus, the coupling process may be continuously and reliably observed. The processor compares the actual position of the module with the target position and outputs the result of this comparison to the alignment device. Thus, a correction and/or an adaption of the actual position of the module and/or the operation range of its functional component may be realized by means of the alignment device. For example, an orientation or position of the module or functional unit may be adjusted or varied until the actual position matches the target position. As a further example, the module may comprise a robotic arm, a two or three axis gantry or the like as a functional component, which is used for handling samples. In this case, the operation range of the robotic arm may be adjusted by means of the alignment device so as to allow a proper operability of the robotic arm.

The detector may be further configured to detect at least one module marker located at the module. With this arrangement, it is possible to go for a relative alignment of the module without precise alignment and calibration of the detector since an in-situ calibration can be realized. For calibration, either the module marker on the module on which the detector is installed or the component marker of the other component can be used.

A type, a size and/or a number of the module marker may be identical to or different from a type of the component marker. Thus, dependent on the intended application, same or different types of markers can be applied as well as the same type of marker but in different number. Thus, basically a broad range of markers can be used depending on the available space and the respective application.

The component marker and the module marker may be located such that the component marker and the module marker are concertedly detectable by the detector. Thus, both markers can be detected in a single field of view or detection range which increases the detection precision.

The component marker and the module marker may each have a predetermined dimension and orientation. Thus, the dimension and orientation may be adapted to the intended application and the available space.

The component marker may be configured to provide a component coordinate system and the module marker may be configured to provide a module coordinate system. The processor may be configured to calculate the position deviation of the module from the target position based on a relative distance between the component coordinate system and the module coordinate system. Thereby, a digital detection result such as an image of the coordinate systems may be obtained and the relative distance and alignment between the two coordinate systems of the module and the component may be calculated. This may be converted into a position correction which is input into the alignment device.

The component marker and the module marker may be configured to allow an in-situ calibration of the detector. Thus, the calculated results for position correction are independent of the detector position and alignment, since image distortion calculation and calibration can be done in situ. For example, using the combination of ArUco marker and calibration pattern, it is only required to determine the relative distance between landmarks and surface. No complex alignment of the detector is necessary, only landmarks and calibration pattern have to be in the detector's field of view.

The position data may include information on a horizontal and/or vertical position of the module. Thus, the orientation of the module may be determined within a three dimensional space.

The detector may be a camera. Thus, a rather cost efficient detection device may be used.

The module may further comprise a distance sensor configured to determine a relative vertical position with respect to the component.

The distance sensor may be configured to determine the relative vertical position based on a distance of reference points at the component from a predetermined module plane. The predetermined module plane may be a handling plane of the module. This detector determines the relative vertical position between reference points from the component to the module such as a handling plane of the module. The distance sensor can be of any kind of sensor suitable to detect a distance, e.g., an optical, capacitive resistive, electromechanical or mechanical distance sensor. Non-exhaustive examples are dial gauges, position sensors, displacement sensors, or any other sensor configured to provide a longitudinal dimension or an angular position as an electric signal. The signal may be analogue such as with a resistance or digital such as with an incremental encoder.

The processor may be configured to calculate the position deviation by means of an algorithm. Thus, an algorithm may be applied to analyze the image made by the detector and calculate the relative distance and alignment between the module and the component. This is converted into a position correction which is input into the fine alignment device of the module.

The module may further comprise an analytical instrument, wherein the alignment device may be configured to align the analytical instrument to the target position based on the position alignment data. Thus, the fine alignment may be realized by slightly adapting the orientation of the analytical instrument.

The alignment device may be configured to move the analytical instrument within a three dimensional space. Thus, the orientation of the analytical instrument may be varied within at least three directions perpendicular to one another.

The target position may be defined by a reference point of or within a reference plane of the component. The reference point of or within a reference plane may be a coordinate system, a plane within such a coordinate system or a known location such as a point in a reference plane. Further, if the orientation of a reference plane within a given three dimensional space is known, a determination of a position relative to the reference plane is allowed. Thus, the relative orientation may be defined according to a given plane facilitating the aligning of the module.

The component may be a transport line of the automated laboratory system or a further module of the automated laboratory system. Thus, the module may be connected to different components.

The target position may be defined by a known location of a point of or within a transport surface of the transport line or a handling plane of the further module. Thus, the target position may be defined by means of a known reference location located at this surface or plane. Further, if the orientation of the transport surface or handling plane within a given three dimensional space is known, a determination of a position relative to the transport surface or handling plane is possible.

The module connector may comprise an engaging member configured to engage a bearing, particularly, a beam or truss, of the component. Thus, the module may be reliably and safely connected to the component. Further, the engaging member provides a coarse alignment of the module.

The engaging member may comprise a hook-shaped protrusion configured to hook on the bearing of the component. Thus, an unintended detachment of the module from the component is reliably prevented.

The engaging member may be arranged at a position at the module such that a vertical position of the module in a state of being connected to the component is defined by the bearing. Thus, the module may be vertically positioned according to the component. Further, tilting of the module and/or pivoting of the module around a vertical axis is realized.

The module may further comprise an infeed configured to receive a component protrusion of the component. This allows a reliable and safe coupling of the module to the component and provides a coarse alignment of the module. Alternatively, the module may further comprise a module protrusion configured to be inserted into a component infeed of the component.

The infeed may be arranged at a position at the module such that a horizontal position of the module in a state of being connected to the component is defined by the component protrusion. Thus, the cooperation of the infeed and the component protrusion provides a coarse horizontal alignment of the module.

The component protrusion may be formed substantially wedge-shaped. Thus, the horizontal alignment is facilitated as even an inclined orientation of the module relative to the component is corrected when further moving the module along the component protrusion.

Alternatively or in addition, a pin or cone having a rounding, truncation or chamfer may be provided at the module or the component which is configured to vertically and laterally guide the module.

The module according to any of the three preceding embodiments, wherein the infeed comprises guiding surfaces configured to engage lateral outer surfaces of the component protrusion. Thus, the module is safely guided to the final position at the component protrusion.

The module may further comprise posts adjustable independent on one another and configured to define a vertical orientation of the module. Thus, a horizontal level of the module may be adjusted. Further, the module may be fixed at a lifted position so as to be decoupled from the floor. Thereby, the progression of vibrations to the analytical instrument are decreased or even prevented.

The module may further comprise casters, particularly swivel casters. Thus, the module may be easily moved.

The module may further comprise a lifting mechanism configured to at least partially lift the module. Thus, the module may be raised and lowered for the coupling and decoupling process. The module may also be lifted by means of an external lifting device such as a lifting stage.

The module may further comprise a frame configured to support an analytical instrument. Thus, the analytical instrument is carried by the frame.

According to another embodiment of the present disclosure, an automated laboratory system is provided comprising a transport line and at least one module according to the above-described details.

According to yet another embodiment of the present disclosure, a method for aligning a module is provided according to the above-described details. The method comprises the following steps: releasably connecting the module to a component of the automated laboratory system; detecting at least one component marker located at the component so as to obtain position data of the module indicating an actual position of the module; calculating a position deviation of the module from a target position defined by the component based on the position data and position alignment data based on the position deviation; and aligning the module to the target position based on the position alignment data.

Thus, an automated fine alignment of the module relative to the component is provided.

Releasably connecting the module to the component of the automated laboratory system may provide a rough or coarse aligning of the module relative to the component. Thus, the method comprises an automated fine alignment based on at least one detector and predetermined marks which optionally can be combined with a coarse alignment such as a manual coarse alignment of the module concertedly occurring when coupling the module to the component. The method for fine alignment uses (mechanical) alignment means including planar (backward-forward and left-right) and vertical (upward-downward) position determination.

The described method of the automated alignment concept enables relative and absolute alignment of modular system components to a transport system. Serviceability and accessibility is ensured through quick connection and disconnection of modular system components within some minutes.

In addition, this method enables continuous monitoring of the alignment with the ability to compensate for drift and thermal expansion or other impact due to, e.g., push or pull or ground movements, e.g., due to thermal shifts within floor level or settling.

By using a point calibration pattern for in situ calibration, the calculated results for position correction are independent of the detector or camera position and alignment, since image distortion calculation and calibration can be done in situ. Using the combination of ArUco marker and calibration pattern it is only required to determine the relative distance between landmarks and surface.

No complex alignment of the detector or camera is necessary, only landmarks and calibration pattern have to be in the detection range or camera's field of view. The detector or camera can be attached to the modular system component and be a part of it or of the transport system if attached there. Furthermore, the detector or camera can also be portable and only be installed during the connection process.

The term "automated laboratory system" as used herein is a broad term and is to be given its ordinary and customary meaning to a person of ordinary skill in the art and is not to be limited to a special or customized meaning. The term specifically may refer, without limitation, to a robotic system for processing a variety of samples in a random flow by different analytical instruments. Such a robotic system encompasses a method for processing the samples using labware such as microtiterplates, filterplates, pipette-tip boxes, sample tubes, caps and the like. The automated laboratory system has a modular architecture, consisting of a central backbone and an arrangement of detachable modules coupled to the backbone. The structure of the automated laboratory system may facilitate the attachment of the modules on both sides of the backbone, meaning that one-sided or double-sided robotic systems can be built.

The term "module" as used herein is a broad term and is to be given its ordinary and customary meaning to a person of ordinary skill in the art and is not to be limited to a special or customized meaning. The term specifically may refer, without limitation, to an individual modular system component of an automated laboratory system configured to carry an analytical instrument for effecting a specific operation on the samples processed by the automated laboratory system, typically in sequence. The analytical instrument can be mounted on a tabletop of the module, underneath the table, or on levels above the tabletop. Typically, the module represents a self-contained processing unit with an analytical instrument and is connectable to the central backbone of the automated laboratory system in a modular and interchangeable fashion.

The term "analytical instrument" as used herein is a broad term and is to be given its ordinary and customary meaning to a person of ordinary skill in the art and is not to be limited to a special or customized meaning. The term specifically may refer, without limitation, to any apparatus or apparatus component operable to execute one or more processing steps/workflow steps on one or more biological samples and/or reagents. The term "processing step" thereby refers to physically executed processing steps such as centrifugation, aliquotation, sample analysis and the like. The term "analytical instrument" covers pre-analytical sample work-cells, post-analytical sample work-cells and also analytical work-cells.

The term "component" as used herein is a broad term and is to be given its ordinary and customary meaning to a person of ordinary skill in the art and is not to be limited to a special or customized meaning. The term specifically may refer, without limitation, to any device to which a module is to be coupled. The term may specifically refer to an individual modular system component of an automated laboratory system or a transport line representing the backbone of the automated laboratory system.

The term "laboratory diagnostic vessel" as used herein is a broad term and is to be given its ordinary and customary meaning to a person of ordinary skill in the art and is not to be limited to a special or customized meaning. The term specifically may refer, without limitation, to any type of container suitable to store a sample or reagent in the field of analytics and more particularly medical analytics. Such vessels are usually designed as tubes.

The term "laboratory diagnostic vessel carrier" as used herein is a broad term and is to be given its ordinary and customary meaning to a person of ordinary skill in the art and is not to be limited to a special or customized meaning. The term specifically may refer, without limitation, to any device configured to hold one or more laboratory diagnostic vessels and to be supplied through a conveying or transport line. Thus, the vessel carrier may be configured as a single vessel carrier suitable to receive a single laboratory diagnostic vessel or a rack suitable to receive a plurality of vessels. Without any restriction, particular embodiments are described with reference to so called test tube holders. Such a test tube holder can hold one single test tube containing a sample or reagent and convey the test tube via a conveyor or transport line to different modules of an automated laboratory system such as an automated sample testing system. The test tube holder comprises a housing with a spring for fixing a test tube, a test tube holder body housing, and a bottom lid housing. The housing with a spring for fixing a test tube has a columnar structure whose center part is roundly bored so as to allow the insertion of the test tube, and is provided with spring parts inside projecting parts extending upward. It is to be noted that the housing with a spring usually has a columnar shape, but it may have any shape as long as the housing can vertically hold the test tube by the spring parts provided equidistantly or equiangularly, and an outer shape of the housing may be a polygonal column shape. The test tube holder body housing has a cylindrical shape, and desirably has a cavity part therein. In the cavity part, a tag with an unique ID number, a weight for stably conveying the test tube, and others are housed. Also, the test tube holder body housing and the bottom lid housing have an outer diameter larger than that of the test tube to be conveyed and smaller than the width of the conveyor line. Note that the shape of the test tube holder body housing and the bottom lid housing may be, for example, a polygonal shape. Even in that case, a maximum length in a cross-sectional direction is desirably smaller than the width of the conveyor or transport line. Particular test tube holder that may be used with the present disclosure are described in EP 2 902 790 A1, the contents thereof concerning the design or construction vessel carriers is incorporated by reference in this application.

The term "module connector" as used herein is a broad term and is to be given its ordinary and customary meaning to a person of ordinary skill in the art and is not to be limited to a special or customized meaning. The term specifically may refer, without limitation, to any device configured to allow a coupling of the module to another component of the automated laboratory system. Particularly, the module connector allows to release the coupling without any destruction of the coupled components either by using a tool or without a tool. Specifically the connector may be or comprise a hitch, latchet, hook, coupler or the like allowing to provide a releasable connection.

The term "releasably connect" or "releasably connecting" as used herein is a broad term and is to be given its ordinary and customary meaning to a person of ordinary skill in the art and is not to be limited to a special or customized meaning. The term specifically may refer, without limitation, to a reversible type of connection. Thus, the connection may encompass a process of coupling or connecting and the releasing of the connection which may be repeated arbitrary times.

The term "detector" as used herein is a broad term and is to be given its ordinary and customary meaning to a person of ordinary skill in the art and is not to be limited to a special or customized meaning. The term specifically may refer, without limitation, to a device, module, machine, or subsystem configured to detect events or changes in its environment and send the information to other electronics, frequently a computer processor. A detector is typically used with other electronics. Particularly, the detector is configured to detect or read information provided by the presence of an information carrier such as a marker. More particularly, the detector is configured to image the marker so as to provide a digital image.

The term "marker" as used herein is a broad term and is to be given its ordinary and customary meaning to a person of ordinary skill in the art and is not to be limited to a special or customized meaning. The term specifically may refer, without limitation, to a machine-readable optical label that could contain information about the item to which it is attached. Particularly, the information may be the identity of the item to which it is attached so as to allow the detection of the presence or absence of the item. This may be realized by a certain pattern serving as marker. The information may be even more detailed on the item's identity such as the type, size, date of manufacturing or the like. Particularly, a target is fitted with a marker which forms a known pattern of known size. Sources of light such as visible or infrared light (active and passive), the visible markers like QR codes (or they can be circular) typically serve as markers for optical tracking. A camera or multiple cameras constantly seek the markers and then use various algorithms (for example, POSIT algorithm) to extract the position of the object from the markers. Such algorithms have to also contend with missing data in case one or more of the markers is outside the camera view or is temporarily obstructed. Markers can be active or passive. The former are typically infrared lights that periodically flash or glow all the time. By synchronizing the time that they are on with the camera, it is easier to block out other IR lights in the tracking area. The latter are retroreflector which reflect the IR light back towards the source almost without scattering.

The term "processor" as used herein is a broad term and is to be given its ordinary and customary meaning to a person of ordinary skill in the art and is not to be limited to a special or customized meaning. The term specifically may refer, without limitation, to an electronic circuit which performs operations on some external data source, usually memory or some other data stream. The term is frequently used to refer to the central processor (central processing unit) in a system, but typical computer systems (especially SoCs) combine a number of specialized "processors".

The term "calculate" as used herein is a broad term and is to be given its ordinary and customary meaning to a person of ordinary skill in the art and is not to be limited to a special or customized meaning. The term specifically may refer, without limitation, to a deliberate process that transforms one or more inputs into one or more results. The term is used to describe a definite arithmetical calculation by using an algorithm.

The term "algorithm" as used herein is a broad term and is to be given its ordinary and customary meaning to a person of ordinary skill in the art and is not to be limited to a special or customized meaning. The term specifically may refer, without limitation, to a finite sequence of well-defined, computer-implementable instructions, typically to solve a class of problems or to perform a computation. Algorithms are always unambiguous and are used as specifications for performing calculations, data processing, automated reasoning, and other tasks. As an effective method, an algorithm can be expressed within a finite amount of space and time, and in a well-defined formal language for calculating a function. Starting from an initial state and initial input (perhaps empty), the instructions describe a computation that, when executed, proceeds through a finite number of well-defined successive states, eventually producing "output" and terminating at a final ending state. The transition from one state to the next is not necessarily deterministic; some algorithms, known as randomized algorithms, incorporate random input.

The term "align" as used herein is a broad term and is to be given its ordinary and customary meaning to a person of ordinary skill in the art and is not to be limited to a special or customized meaning. The term specifically may refer, without limitation, to a process of arranging a constructional member or device according to a pre-defined orientation within a three dimensional space. The pre-defined orientation may be given by another device serving as a reference. Thus, the device is arranged according to a reference defining the target position for the device to be aligned.

Further, this term also refers to an adjustment of the operation range of the module as well as its functional components such as a potential robotic arm or any other handling device. As such, the functional component of the module may be adjusted in its operation range so as to operate without any obstruction or to operate with minimizing the size or number of any obstacles.

The term "alignment device" as used herein is a broad term and is to be given its ordinary and customary meaning to a person of ordinary skill in the art and is not to be limited to a special or customized meaning. The term specifically may refer, without limitation, to any device configured to provide or carry out the aligning as described above. Thus, the alignment device may be a mechanical and/or electric alignment device.

The term "coordinate system" as used herein is a broad term and is to be given its ordinary and customary meaning to a person of ordinary skill in the art and is not to be limited to a special or customized meaning. The term specifically may refer, without limitation, to a system that uses one or more numbers, or coordinates, to uniquely determine the position of the points or other geometric elements on a manifold such as Euclidean space. The order of the coordinates is significant, and they are sometimes identified by their position in an ordered tuple and sometimes by a letter, as in "the x-coordinate". The coordinates are taken to be real numbers in elementary mathematics, but may be complex numbers or elements of a more abstract system such as a commutative ring. The use of a coordinate system allows problems in geometry to be translated into problems about numbers and vice versa. The term may specifically refer to a Cartesian coordinate system such as a three dimensional Cartesian coordinate system which is a coordinate system that specifies each point uniquely in a plane by a set of numerical coordinates, which are the signed distances to the point from two fixed perpendicular oriented lines, measured in the same unit of length. Each reference line is called a coordinate axis or just axis (plural axes) of the system, and the point where they meet is its origin, at ordered pair (0, 0). The coordinates can also be defined as the positions of the perpendicular projections of the point onto the two axes, expressed as signed distances from the origin.

The term "vertical" as used herein is a broad term and is to be given its ordinary and customary meaning to a person of ordinary skill in the art and is not to be limited to a special or customized meaning. The term specifically may refer, without limitation, to an orientation parallel to a direction of gravity.

The term "horizontal" as used herein is a broad term and is to be given its ordinary and customary meaning to a person of ordinary skill in the art and is not to be limited to a special or customized meaning. The term specifically may refer, without limitation, to an orientation perpendicular to a direction of gravity.

The term "distance sensor" as used herein is a broad term and is to be given its ordinary and customary meaning to a person of ordinary skill in the art and is not to be limited to a special or customized meaning. The term specifically may refer, without limitation, to a sensor that facilitates measurement of a distance of an object from a reference point or a variation of a length. The result may be output as a mechanical position. A distance sensor may indicate absolute position (location) or relative position (displacement), in terms of linear travel, rotational angle, or three-dimensional space. Common types of distance sensor s include capacitive displacement sensor, eddy-current sensor, hall effect sensor, inductive sensor, laser Doppler vibrometer (optical), linear variable differential transformer (LVDT), photodiode array, piezo-electric transducer (piezo-electric), absolute encoder, incremental encoder, linear encoder, rotary encoder, potentiometer, proximity sensor (optical), string potentiometer (also known as string potentiometer, string encoder, cable position transducer), ultrasonic sensor and optical sensors such as a camera based distance sensor.

The term "handling plane" as used herein is a broad term and is to be given its ordinary and customary meaning to a person of ordinary skill in the art and is not to be limited to a special or customized meaning. The term specifically may refer, without limitation, to a plane of the module where the handling of the samples takes place. The handling plane may be intended to provide a stepless transition to a reference plane of the component to which the module is coupled such as a transport surface of a transport line.

The term "engaging member" as used herein is a broad term and is to be given its ordinary and customary meaning to a person of ordinary skill in the art and is not to be limited to a special or customized meaning. The term specifically may refer, without limitation, to any constructional member that is configured to make one part of a device fit into or onto a part of another device so as to be integrally coupled thereto. The engaging may be realized as a positive locking fit. The engaging may be realized as a releasable coupling.

The term "infeed" as used herein is a broad term and is to be given its ordinary and customary meaning to a person of ordinary skill in the art and is not to be limited to a special or customized meaning. The term specifically may refer, without limitation, to any part of a device configured to receive another part of another device when both devices are moved towards one another and coupled. Particularly, the other part of the other device may be inserted into the infeed so as to provide a guided movement for the device having the infeed.

The term "wedge-shaped" as used herein is a broad term and is to be given its ordinary and customary meaning to a person of ordinary skill in the art and is not to be limited to a special or customized meaning. The term specifically may refer, without limitation, to a shape like a wedge. The term "wedge" may refer to an object having a tapered shape. More particularly, the object may have a substantially triangular shape such as an object with one pointed edge and one thick edge.

The term "adjustable post" as used herein is a broad term and is to be given its ordinary and customary meaning to a person of ordinary skill in the art and is not to be limited to a special or customized meaning. The term specifically may refer, without limitation, to a column that may vary its length. Particularly, the post may be designed to be able to mechanically telescope to about twice its shortest length. The post may use removable pins for coarse adjustment and a jack screw for fine adjustments, but many variations exist.

The term "caster" as used herein is a broad term and is to be given its ordinary and customary meaning to a person of ordinary skill in the art and is not to be limited to a special or customized meaning. The term specifically may refer, without limitation, to an undriven, single, double, or compound wheel that is designed to be attached to the bottom of a larger object (the "vehicle") to enable that object to be moved. They are available in various sizes, and are commonly made of rubber, plastic, nylon, aluminum, or stainless steel. Casters may be fixed to roll along a straight line path, or mounted on a pivot or pintle such that the wheel will automatically align itself to the direction of travel. A basic, rigid caster consists of a wheel mounted to a stationary fork. The orientation of the fork, which is fixed relative to the vehicle, is determined when the caster is mounted to the vehicle. Rigid casters tend to restrict vehicle motion so that the vehicle travels along a straight line. Like the simpler rigid caster, a swivel caster incorporates a wheel mounted to a fork, but an additional swivel joint above the fork allows the fork to freely rotate about 360°, thus enabling the wheel to roll in any direction. This makes it possible to easily move the vehicle in any direction without changing its orientation.

Further disclosed and proposed herein is a computer program including computer-executable instructions for performing the method according to the present disclosure in one or more of the embodiments enclosed herein when the program is executed on a computer or computer network. Specifically, the computer program may be stored on a computer-readable data carrier and/or on a computer-readable storage medium.

As used herein, the terms "computer-readable data carrier" and "computer-readable storage medium" specifically may refer to non-transitory data storage means, such as a hardware storage medium having stored thereon computer-executable instructions. The computer-readable data carrier or storage medium specifically may be or may comprise a storage medium such as a random-access memory (RAM) and/or a read-only memory (ROM).

Thus, specifically, one, more than one or even all of method steps a) to d) as indicated above may be performed by using a computer or a computer network, typically by using a computer program.

Further disclosed and proposed herein is a computer program product having program code means, in order to perform the method according to the present disclosure in one or more of the embodiments enclosed herein when the program is executed on a computer or computer network. Specifically, the program code means may be stored on a computer-readable data carrier and/or on a computer-readable storage medium.

Further disclosed and proposed herein is a data carrier having a data structure stored thereon, which, after loading into a computer or computer network, such as into a working memory or main memory of the computer or computer network, may execute the method according to one or more of the embodiments disclosed herein.

Further disclosed and proposed herein is a computer program product with program code means stored on a machine-readable carrier, in order to perform the method according to one or more of the embodiments disclosed herein, when the program is executed on a computer or computer network. As used herein, a computer program product refers to the program as a tradable product. The product may generally exist in an arbitrary format, such as in a paper format, or on a computer-readable data carrier and/or on a computer-readable storage medium. Specifically, the computer program product may be distributed over a data network.

Finally, disclosed and proposed herein is a modulated data signal which contains instructions readable by a computer system or computer network, for performing the method according to one or more of the embodiments disclosed herein.

Referring to the computer-implemented embodiments of the disclosure, one or more of the method steps or even all of the method steps of the method according to one or more of the embodiments disclosed herein may be performed by using a computer or computer network. Thus, generally, any of the method steps including provision and/or manipulation of data may be performed by using a computer or computer network. Generally, these method steps may include any of the method steps, typically except for method steps requiring manual work, such as providing the samples and/or certain aspects of performing the actual measurements.

Specifically, further disclosed herein are:
a computer or computer network comprising at least one processor, wherein the processor is adapted to perform the method according to one of the embodiments described in this description,
a computer loadable data structure that is adapted to perform the method according to one of the embodiments described in this description while the data structure is being executed on a computer,
a computer program, wherein the computer program is adapted to perform the method according to one of the embodiments described in this description while the program is being executed on a computer,
a computer program comprising program means for performing the method according to one of the embodiments described in this description while the computer program is being executed on a computer or on a computer network,
a computer program comprising program means according to the preceding embodiment, wherein the program means are stored on a storage medium readable to a computer,
a storage medium, wherein a data structure is stored on the storage medium and wherein the data structure is adapted to perform the method according to one of the embodiments described in this description after having been loaded into a main and/or working storage of a computer or of a computer network, and a computer program product having program code means, wherein the program code means can be stored or are stored on a storage medium, for performing the method according to one of the embodiments described in this description, if the program code means are executed on a computer or on a computer network.

Summarizing and without excluding further possible embodiments, the following embodiments may be envisaged:

Embodiment 1: A module for an automated laboratory system, comprising
- a module connector configured to releasably connect to a component of the automated laboratory system,
- a detector at least configured to detect at least one component marker located at the component so as to obtain position data of the module indicating an actual position of the module,
- a processor configured to calculate a position deviation of the module from a target position defined by the component based on the position data and to calculate position alignment data based on the position deviation, and
- an alignment device configured to align the module or its functional unit to the target position based on the position alignment data.

Embodiment 2: The module according to the preceding embodiment, wherein the detector is further configured to detect at least one module marker located at the module.

Embodiment 3: The module according to the preceding embodiment, wherein a type, a size and/or a number of the module marker are identical to or different from a type of the component marker.

Embodiment 4: The module according to any of the two preceding embodiments, wherein the component marker and the module marker are located such that the component marker and the module marker are concertedly detectable by the detector.

Embodiment 5: The module according to any of the three preceding embodiments, wherein the component marker and the module marker each have a predetermined dimension and orientation.

Embodiment 6: The module according to any of the four preceding embodiments, wherein the component marker is configured to provide a component coordinate system and the module marker is configured to provide a module coordinate system, wherein the processor is configured to calculate the position deviation of the module from the target position based on a relative distance between the component coordinate system and the module coordinate system.

Embodiment 7: The module according to any of the five preceding embodiments, wherein the component marker and the module marker are configured to allow an in-situ calibration of the detector.

Embodiment 8: The module according to any preceding embodiment, wherein the position data include information on a horizontal and/or vertical position of the module.

Embodiment 9: The module according to any preceding embodiment, wherein the detector is a camera.

Embodiment 10: The module according to any preceding embodiment, further comprising a distance sensor configured to determine a relative vertical position with respect to the component.

Embodiment 11: The module according to the preceding embodiment, wherein the distance sensor is configured to determine the relative vertical position based on a distance of reference points at the component from a predetermined module plane.

Embodiment 12: The module according to the preceding embodiment, wherein the predetermined module plane is a handling plane of the module.

Embodiment 13: The module according to any of the three preceding embodiments, wherein the distance sensor is an optical, capacitive resistive, electromechanical or mechanical distance sensor.

Embodiment 14: The module according to any preceding embodiment, wherein the processor is configured to calculate the position deviation by means of an algorithm.

Embodiment 15: The module according to any preceding embodiment, further comprising an analytical instrument, wherein the alignment device is configured to align the analytical instrument to the target position based on the position alignment data.

Embodiment 16: The module according to the preceding embodiment, wherein the alignment device is configured to move the analytical instrument within a three dimensional space.

Embodiment 17: The module according to any preceding embodiment, wherein the target position is defined by a reference point of or within a reference plane of the component.

Embodiment 18: The module according to any preceding embodiment, wherein the component is a transport line of the automated laboratory system or a further module of the automated laboratory system.

Embodiment 19: The module according to the preceding embodiment, wherein the target position is defined by a point of or within a transport surface of the transport line or a handling plane of the further module.

Embodiment 20: The module according to any preceding embodiment, wherein the module connector comprises an engaging member configured to engage a bearing, particularly, a beam or truss, of the component.

Embodiment 21: The module according to the preceding embodiment, wherein the engaging member comprises a hook-shaped protrusion configured to hook on the bearing of the component.

Embodiment 22: The module according to any of the two preceding embodiments, wherein the engaging member is arranged at a position at the module such that a vertical position of the module in a state of being connected to the component is defined by the bearing.

Embodiment 23: The module according to any preceding embodiment, further comprising an infeed configured to receive a component protrusion of the component or further comprising a module protrusion configured to be inserted into a component infeed of the component.

Embodiment 24: The module according to the preceding embodiment, wherein the infeed is arranged at a position at the module such that a horizontal position of the module in a state of being connected to the component is defined by the component protrusion.

Embodiment 25: The module according to any of the two preceding embodiments, wherein the component protrusion is formed substantially wedge-shaped.

Embodiment 26: The module according to any of the three preceding embodiments, wherein the infeed comprises guiding surfaces configured to engage lateral outer surfaces of the component protrusion.

Embodiment 27: The module according to any preceding embodiment, further comprising posts adjustable independent on one another and configured to define a vertical orientation of the module.

Embodiment 28: The module according to any preceding embodiment, further comprising casters, particularly, swivel casters.

Embodiment 29: The module according to any preceding embodiment, further comprising a lifting mechanism configured to at least partially lift the module.

Embodiment 30: The module according to any preceding embodiment, further comprising a frame configured to support an analytical instrument.

Embodiment 31: An automated laboratory system comprising a transport line and at least one module according to any preceding embodiment.

Embodiment 32: A method for aligning a module according to any one of embodiments 1 to 30, comprising
- releasably connecting the module to a component of the automated laboratory system,
- detecting at least one component marker located at the component so as to obtain position data of the module indicating an actual position of the module,
- calculating a position deviation of the module from a target position defined by the component based on the position data and position alignment data based on the position deviation, and
- aligning the module to the target position based on the position alignment data.

Embodiment 33: The method according to the preceding embodiment, wherein releasably connecting the module to the component of the automated laboratory system provides a rough aligning of the module relative to the component.

In order that the embodiments of the present disclosure may be more readily understood, reference is made to the following examples, which are intended to illustrate the disclosure, but shall not be construed, whatsoever, to limit the scope thereof.

FIG. 1 shows a perspective view of an automated laboratory system 100. The automated laboratory system 100 is configured to process a plurality or variety of samples 102 in a random flow by different process or analytical instruments 104. The automated laboratory system 100 encompasses a method for processing the samples 102 using labware such as microtiterplates, filterplates, pipette-tip boxes and the like (not shown). The automated laboratory system 100 has a modular architecture, consisting of several components 106, 108. Particularly, the automated laboratory system 100 has a central backbone 108 and an arrangement of detachable modules 106 coupled to the backbone 108. The central backbone 108 may be a transport line for conveying the samples 102 to and away from the modules 106. The transport line can be of conveyor type, mechanically driven carrier, magnetic transport, self-propelled carrier, individual single sample transport, rack transport or any other kind of sample transport.

The modules 106 carry the analytical instruments 104 for effecting a specific operation on the samples 102, such as in sequence. The analytical instruments 104 can be mounted on a tabletop 110 of the modules 106, underneath the tabletop 110, or on levels above the tabletop 110 as further described below. The structure of the automated laboratory system 100 facilitates the attachment of the modules 106 on both sides of the backbone 108, meaning that one-sided or double-sided automated laboratory system 100 can be built. Typically, the modules 106 represent self-contained processing units with analytical instruments 104, and are connectable to the central backbone 108 in a modular and interchangeable fashion. The analytical instruments 104 may be housed by a housing 112 of the module 106, which at least partially encloses the tabletop 110.

Figure 2:
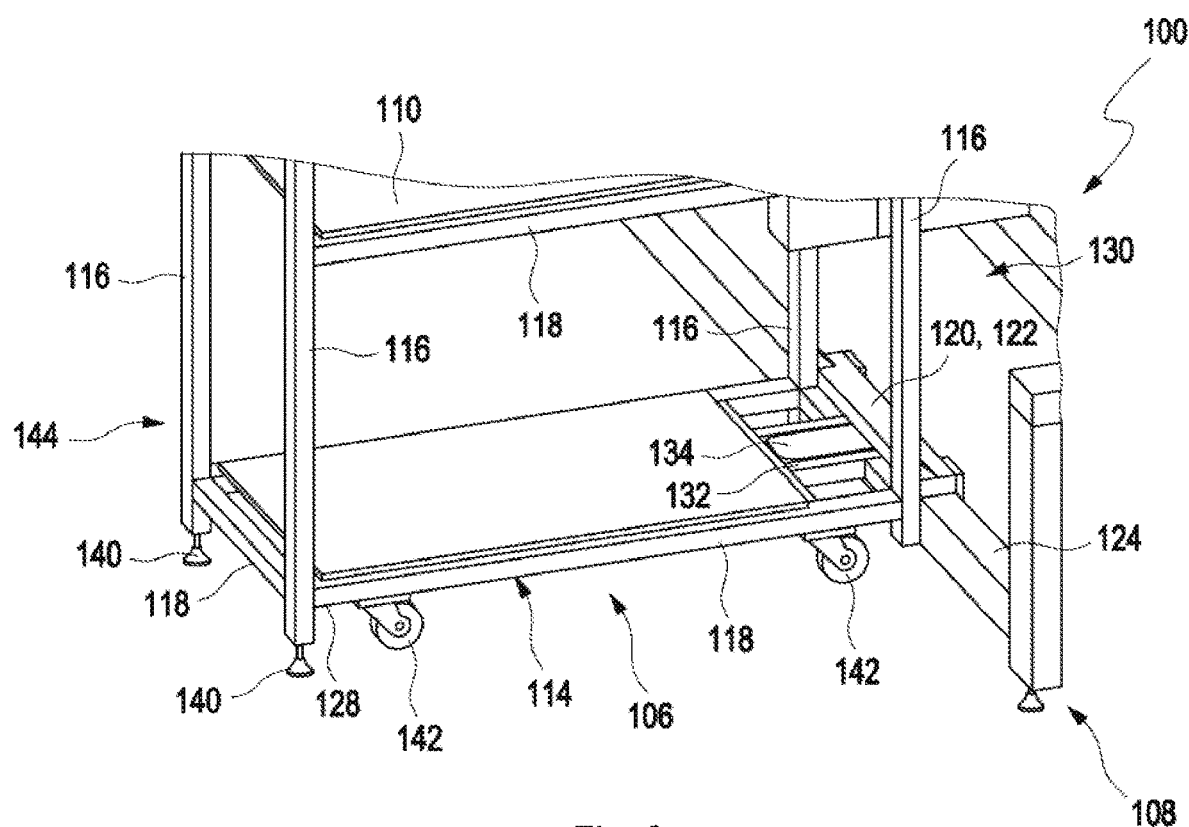
FIG. 2 shows a perspective view of a portion of a module.

FIG. 2 shows a perspective view of a portion of a module 106. The module 106 comprises a frame 114 supporting the tabletop 110. The frame 114 comprises vertical frame members 116 and horizontal frame members 118. For example, four vertical frame members 116 and six horizontal frame members 118 are arranged so as to provide a substantially rectangular or cuboid shape for the frame 114. The number of vertical and horizontal frame members 116, 118 may vary depending on the respective application. The vertical and horizontal frame members 116, 118 may be beams having a rectangular or square-shaped cross-section. The frame 114 is configured to support the housing 112. For example, the housing may be releasably mounted to the frame 114. The frame 114 may designed in any other way such as depending on the respective application of the module 106.

Figure 3:
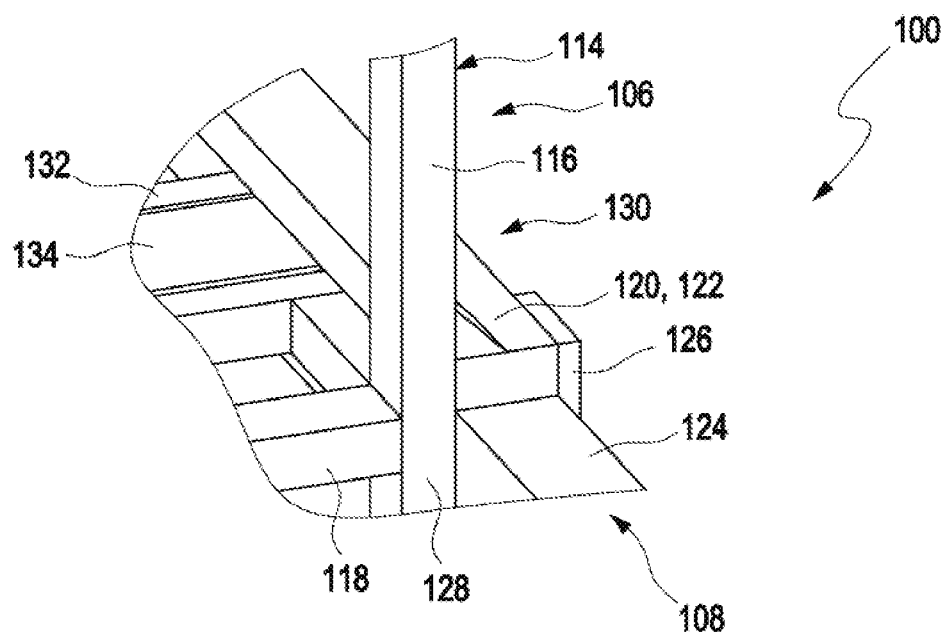
FIG. 3 shows an enlarged lateral view of a portion of the module in a coupled state.
Figure 4:
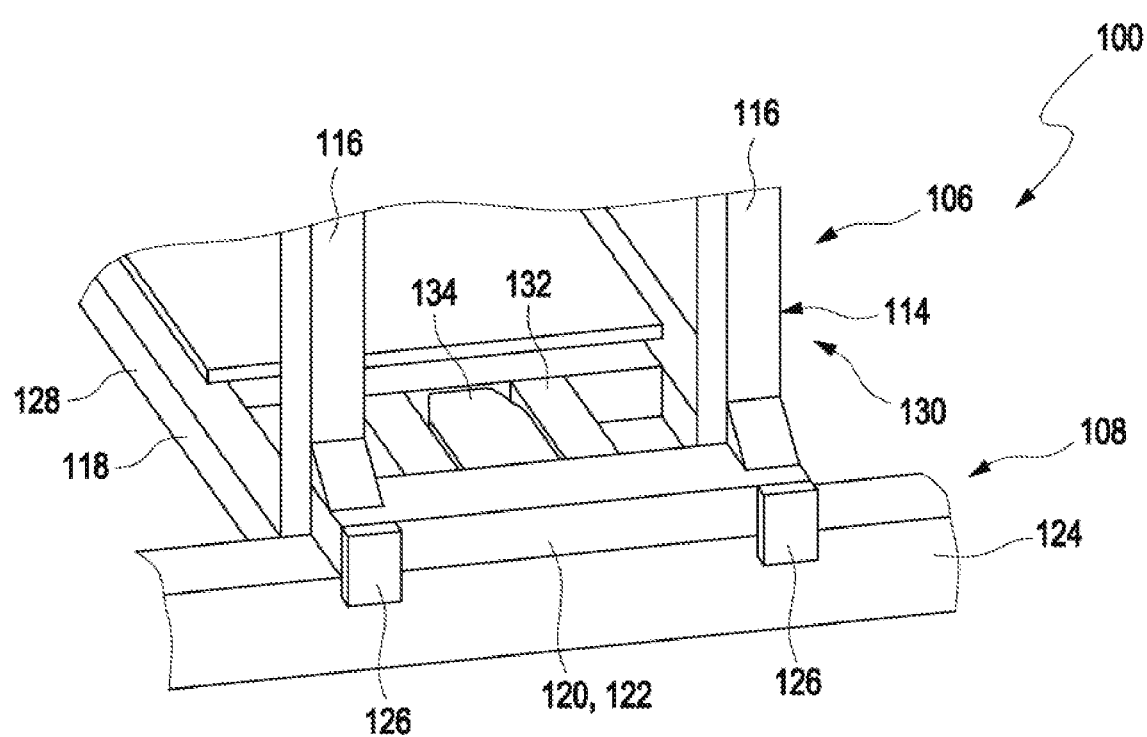
FIG. 4 shows an enlarged rear view of a portion of the module in a coupled state.

FIG. 3 shows an enlarged lateral view of a portion of the module 106 in a coupled state. FIG. 4 shows an enlarged rear view of a portion of the module 106 in a coupled state. The module 106 further comprises a module connector 120 configured to releasably connect to a component 106, 108 of the automated laboratory system 110. The module connector 120 comprises an engaging member 122 configured to engage a bearing 124 such as a beam or truss of the component 106, 108 such as the backbone 108. The engaging member 122 comprises a hook-shaped protrusion 126 configured to hook on the bearing 124 of the component 106, 108. The engaging member 122 is arranged at a position at the module 106 such that a vertical position of the module 106 in a state of being connected to the component 106, 108 is defined by the bearing 124. In the present embodiment, the module connector 120 and the engaging member 122, respectively, are arranged adjacent a lower end 128 of the frame 114 at a rear side 130 of the module 106. The module connector 120 protrudes from the frame 114. The bearing 124 is referenced to the transport plane of the transport line 108 for vertical alignment and tilting of the module 106. Optionally, the bearing 124 can be mechanically decoupled from the transport line 108 to prevent vibration coupling.

Figure 5:
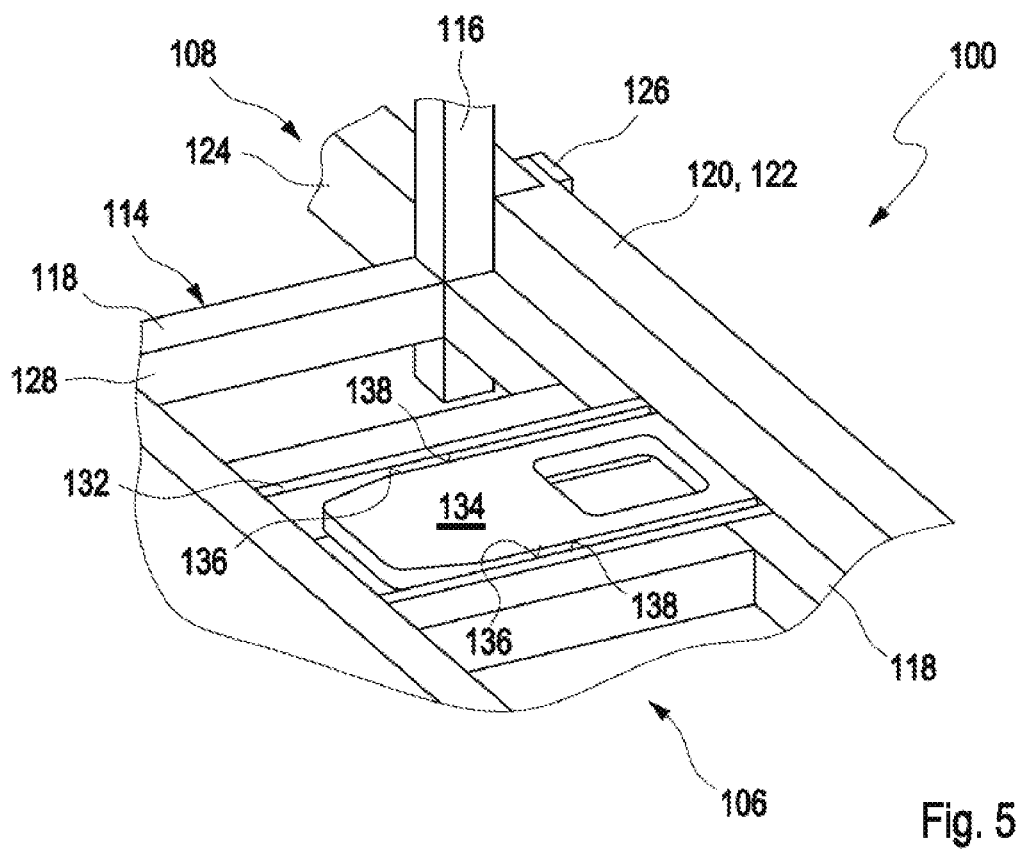
FIG. 5 shows an enlarged view of a portion of the module in a coupled state.

FIG. 5 shows an enlarged view of a portion of the module 106 in a coupled state. The module 106 further comprises an infeed 132 configured to receive a component protrusion 134 of the component 106, 108. The infeed 132 is arranged at a position at the module 106 such that a horizontal position of the module 106 in a state of being connected to the component 106, 108 is defined by the component protrusion 134. In the present embodiment, the infeed 132 is horizontally arranged in a central horizontal portion of the frame 114. Further, the infeed 132 is vertically arranged between the engaging member 122 and the lower end 128 of the frame 114. As shown in FIG. 5, the component protrusion 134 is formed substantially wedge-shaped which facilitates a sliding movement of the infeed 132 onto the component protrusion 134. For this purpose, the infeed 132 comprises guiding surfaces 136 configured to engage lateral outer surfaces 138 of the component protrusion 134. The wedge-shaped protrusion 134 is formed with a predefined play to the infeed 132, is positioned at the bearing 124 and referenced to the target position of the module 106 at the transport line 108 regarding left right orientation. The module 106 may optionally further comprise a tapered pin in horizontal or vertical orientation engaging into a bearing hole and locked against each other.

Figure 6:
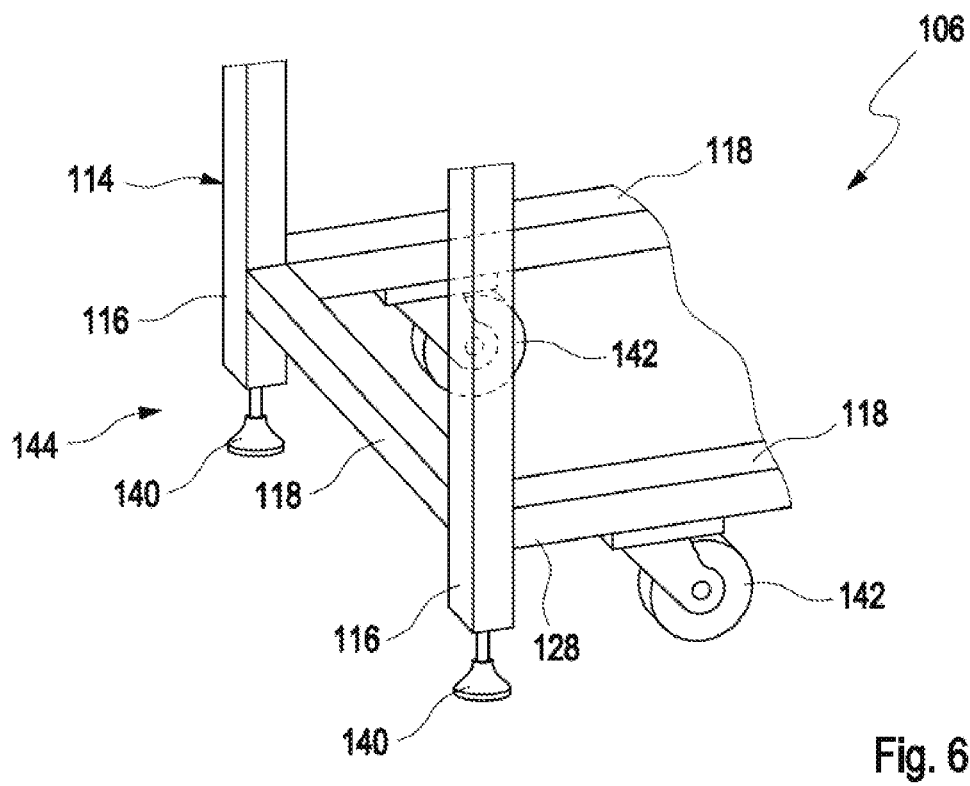
FIG. 6 shows an enlarged lateral view of a portion of the module in a coupled state.

FIG. 6 shows an enlarged lateral view of a portion of the module 106 in a coupled state. The module 106 further comprises posts 140 adjustable independent on one another and configured to define a vertical orientation of the module 106. The adjustable posts 140 also allow tilting of the module when connected to the backbone 108. For this reason, the module 106 comprises at least two adjustable posts 140. For example, four adjustable posts 140 are present. The adjustable posts 140 are slidably received within the vertical frame members 116. The module 106 further comprises casters 142. For example, four casters 142 are present. At least some of the casters 142 may be swivel casters. For example, two casters 142 at a front side 144 of the frame 114 are swivel casters.

Figure 7:
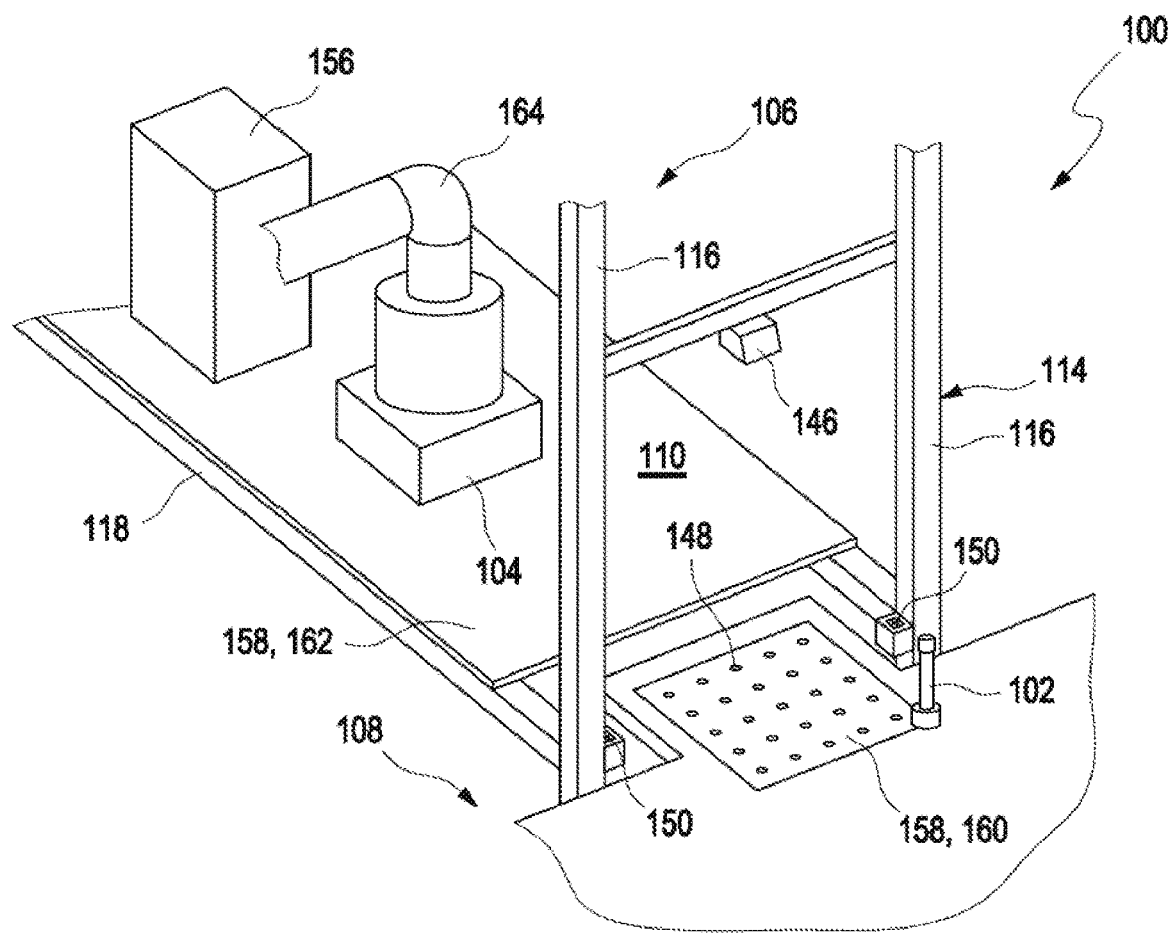
FIG. 7 shows a perspective view of a portion of the module.
Figure 8:
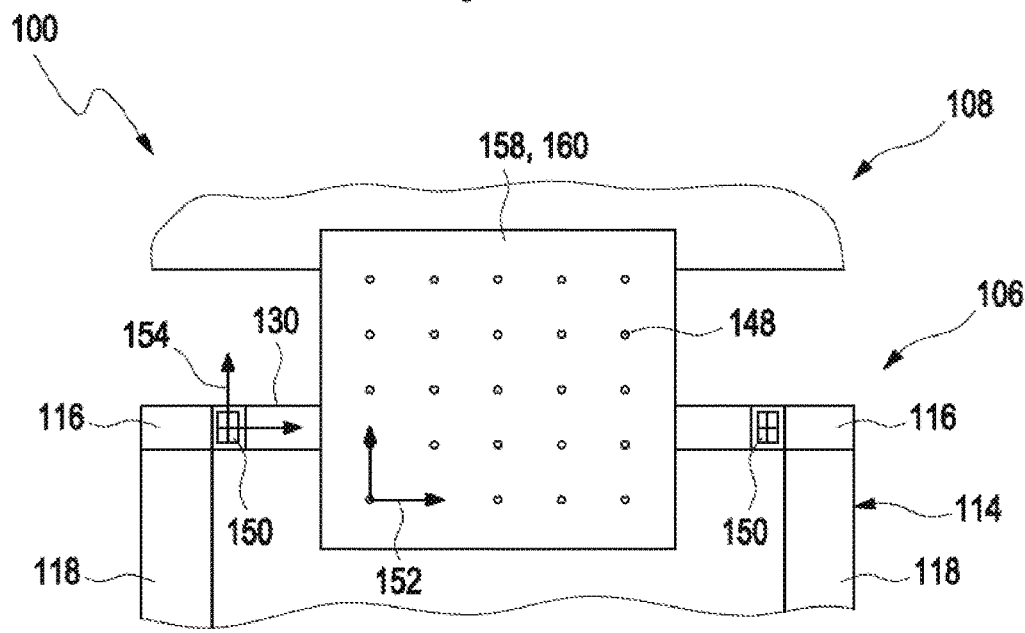
FIG. 8 shows a top view of a portion of the module.

FIG. 7 shows a perspective view of a portion of the module 106. FIG. 8 shows a top view of a portion of the module 106. The module 106 further comprises a detector 146. The detector 146 is at least configured to detect at least one component marker 148 located at the component 106, 108 so as to obtain position data of the module 106 indicating an actual position of the module 106. The position data include information on a horizontal and/or vertical position of the module 106. The detector 146 may be a camera. The camera may be provided with visible or invisible illumination if required and is attached to the module 106 and directed towards the transport line 108. The detector 146 is further configured to detect at least one module marker 150 located at the module 106. The component marker 148 and the module marker 150 are located such that the component marker 148 and the module marker 150 are concertedly detectable by the detector 146. With other words, the component marker 148 and the module marker 150 are both located to be in the detection range or field of view of the detector 146. The component marker 148 and the module marker 150 each have a predetermined dimension and orientation. The predetermined dimension and orientation of the component marker 148 and the module marker 150 may be identical but do not need to be identical. The component marker 148 is configured to provide a component coordinate system 152 and the module marker 150 is configured to provide a module coordinate system 154. In the present embodiment, the module markers 150 are located at a transition of the lower vertical frame members 116 and horizontal frame members 118 at the rear side 130 of the module 106. The component marker 148 may provide a calibration pattern such as a point or dot pattern. The calibration pattern is not limited to dot pattern, it can also be realized as cross pattern, checkerboard or any kind of point pattern which could be analyzed by image processing.

The size and type of the used markers 148, 150 depend on the available space on the object on which they are placed and on the required quality and capabilities of compensation. The markers 148 can be of ArUco type or of other kind of patterns, e.g., point or checkerboard patterns with known dimensions and orientations. These types of marker can offer 2d-calibration and position determination with a camera as well as cross checks. For example, dot patterns a minimum number of well arranged dots needs to be given. In addition, ArUco marker provides identification. ArUco markers are binary square fiducial markers that can be used for camera pose estimation. Their main benefit is that their detection is robust, fast and simple.

The module 106 further comprises a processor 156 configured to calculate a position deviation of the module 106 from a target position defined by the component 106, 108 based on the position data and to calculate position alignment data based on the position deviation. Particularly, the processor 156 is configured to calculate the position deviation of the module from the target position based on a relative distance between the component coordinate system 152 and the module coordinate system 154. The processor 156 is configured to calculate the position deviation by means of an algorithm. The target position is defined by a reference point of or within a reference plane 158 of the component 106, 108. As the component 106, 108 may be the transport line 108 of the automated laboratory system 100 or a further module 106 of the automated laboratory system 100, the target position may be defined by a point of or within a transport surface 160 of the transport line 108 or a handling plane 162 of the further module 106. Thus, the reference plane 158 may be the transport surface 160 or the tabletop 110 used as handling plane 162 of such a module 106.

The module 106 further comprises an alignment device 164 configured to align the module 106 to the target position based on the position alignment data. More particularly, the alignment device 164 is configured to align the analytical instrument 104 to the target position based on the position alignment data. Particularly, the alignment device 164 is configured to move the analytical instrument 104 within a three dimensional space. For example, the alignment device 164 is a mechanical alignment device such as a so-called xyz-stage. It is explicitly stated that the alignment device 164 may align itself or any other functional component of the module 106 according to the target position so as to increase or maximize the operation range thereof.

Figure 9:
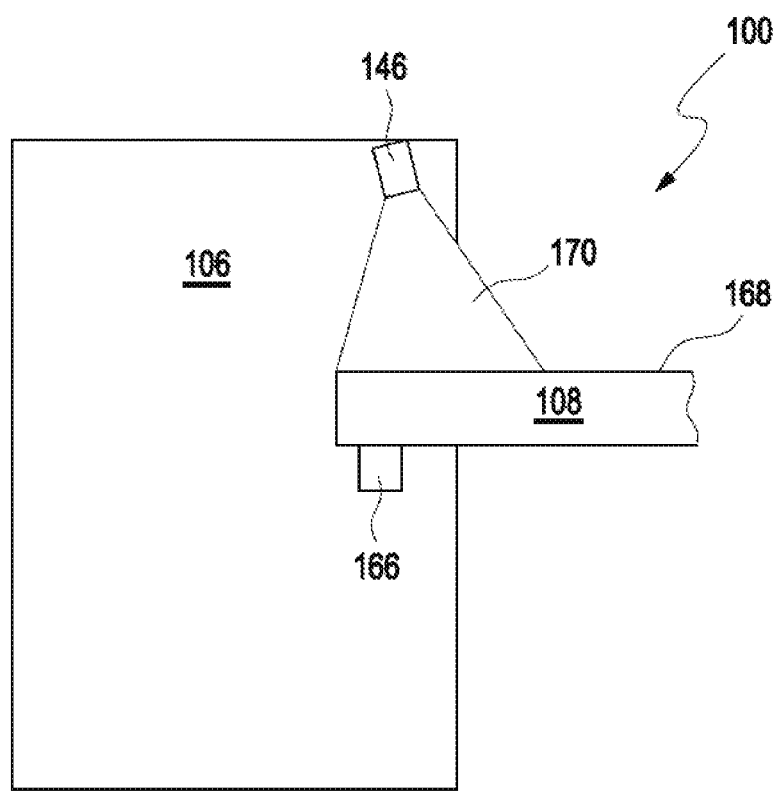
FIG. 9 shows a cross-sectional view of a portion of the module.

FIG. 9 shows a cross-sectional view of a portion of the module 106. The module 106 further comprises an optional distance sensor 166 configured to determine a relative vertical position with respect to the component 106, 108. The distance sensor 166 may be an optical or capacitive distance sensor. Particularly, the distance sensor 166 is configured to determine the relative vertical position based on a distance of reference points 168 at the component 106, 108 from a predetermined module plane 168. The predetermined module plane 168 may be the handling plane 162 of the module 106. Basically, in order to determine the vertical position, the camera setup of the detector 146 with appropriate markers 148, 150 can be used as well. FIG. 9 also shows an example of the detection range or field of view 170 of the detector 146 on the predetermined module plane 168.

Figure 10:
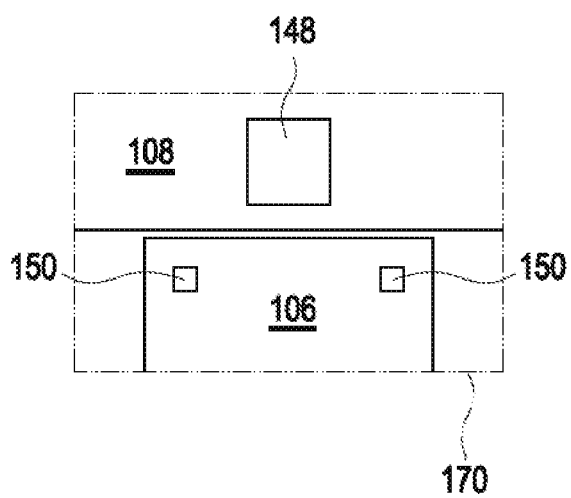
FIGS. 10A and 10B show different arrangements of markers applicable with the present disclosure.
Figure 10:
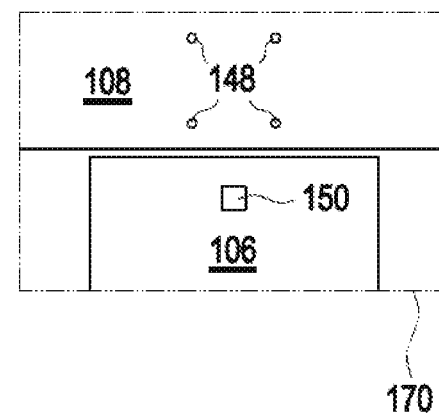

FIGS. 10A and 10B show different arrangements of markers applicable with the present disclosure. As will be explained in further detail, a type, a size and/or a number of the module marker 150 may be identical to or different from a type of the component marker 148. In FIGS. 10A and 10B, the detection range or field of view 170 of the detector 146 is shown. Further, FIGS. 10A and 10B show portions of the module 106 and the transport line 108 to which the module marker 150 and the component marker 148 are attached. FIG. 10A shows one large component marker 148 attached to the transport line 108 and two module markers 150 attached to the module 106. FIG. 10B shows one component marker 148, which is formed by four dots arranged in a square-shaped pattern and which is attached to the transport line 108, and one module marker 150 attached to the module 106.

There are multiple options to arrange the markers 148, 150. If a camera with factory calibration is used, only the component marker 148 on the component such as the transport line 108 is sufficient. This means, no module marker 150 or on any other component, on which the camera is installed, is needed. For example, the module 106 is not provided with a module marker 148 but there is a component marker 150 on the other component 106, 108, e.g., the transport line. Consequence is that the camera has to be mounted rugged and has to be precisely aligned and calibrated, e.g., factory calibration, to the component on which it is installed. With this arrangement, relative and absolute alignment is possible by imaging and analyzing the component marker 150 on the other component 106, 108 with the knowledge of the exact position and calibration of the camera. However, any minor changes in the cameras alignment versus the other component 106, 108 may result in a calibration update procedure.

For this reason, it may be advantageous to provide markers on both components. For example, as described above, there is arranged at least one module marker 150 on the module 106 and there is arranged at least one component marker 148 on the transport line 108. Basically, the type of marker can be of same or different kind but must consist of at least three points. The number of points in the marker determines the quality and capabilities of calibration and alignment. With this arrangement and an appropriate set of markers, it is possible to go for a relative alignment to the module 106 without precise alignment and calibration of the camera since an in-situ calibration can be realized. For calibration, either the marker 150 on the component on which the camera is installed can be used or the component marker 148 of the other component.

Figure 11:
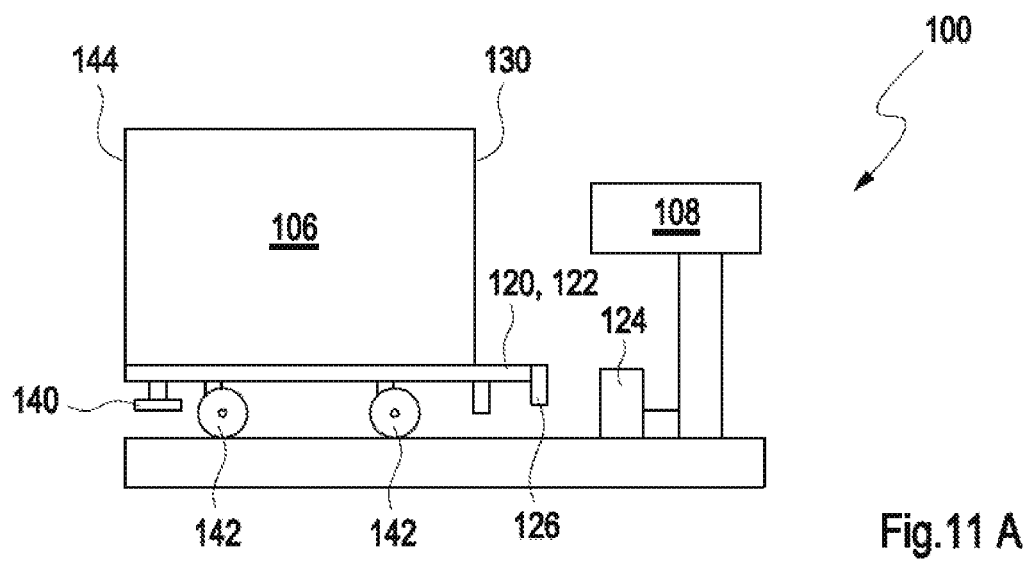
FIGS. 11A to 11H show an operation of coupling the module to a component.
Figure 11:
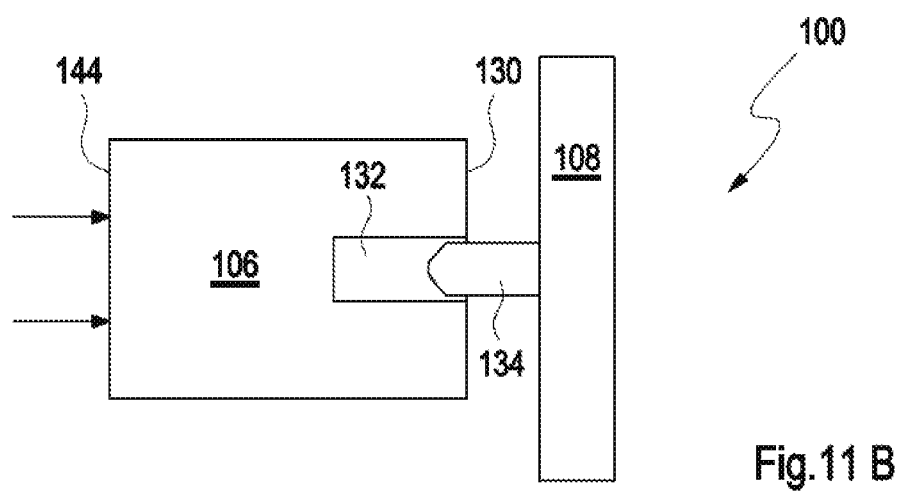
Figure 11:
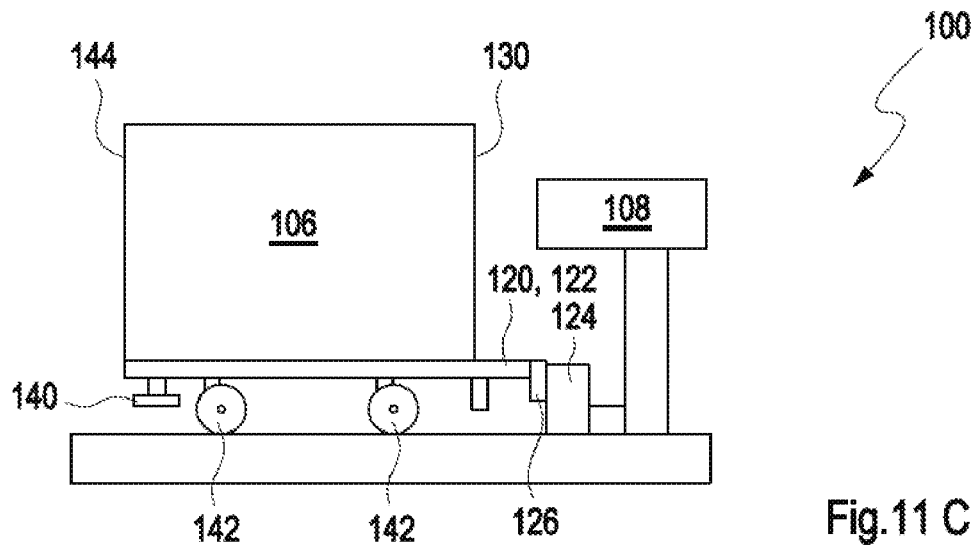
Figure 11:
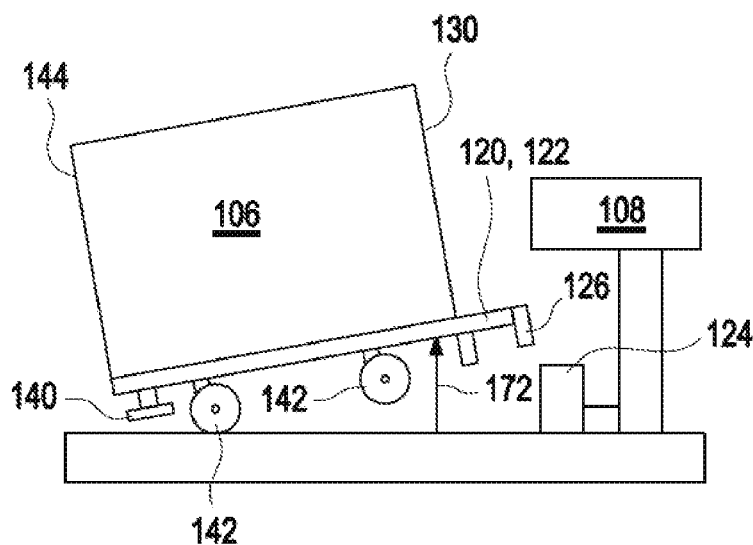
Figure 11:
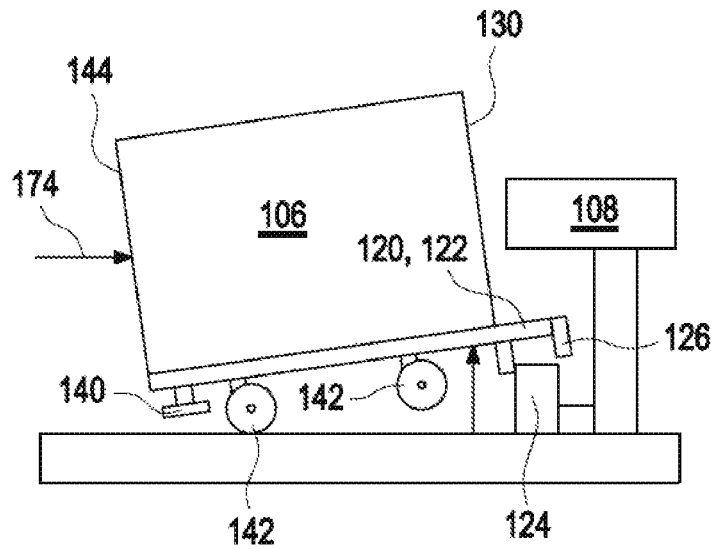
Figure 11:
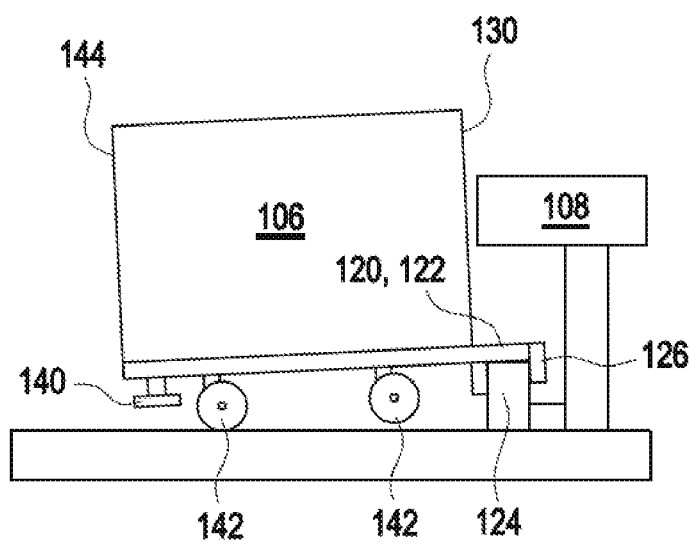
Figure 11:
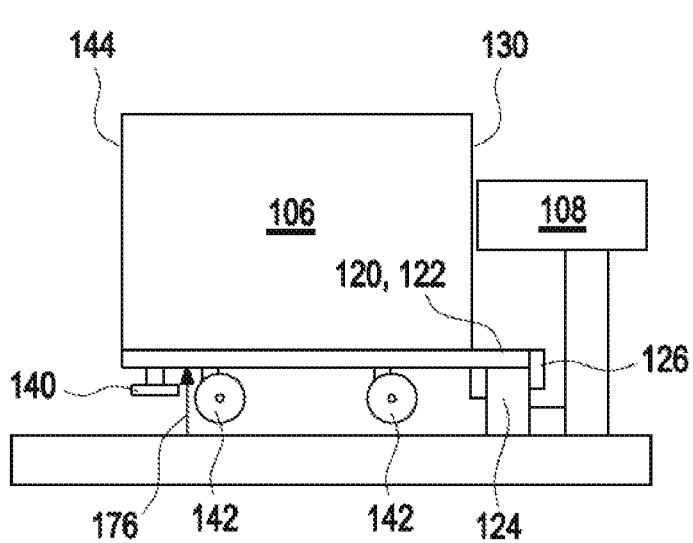
Figure 11:
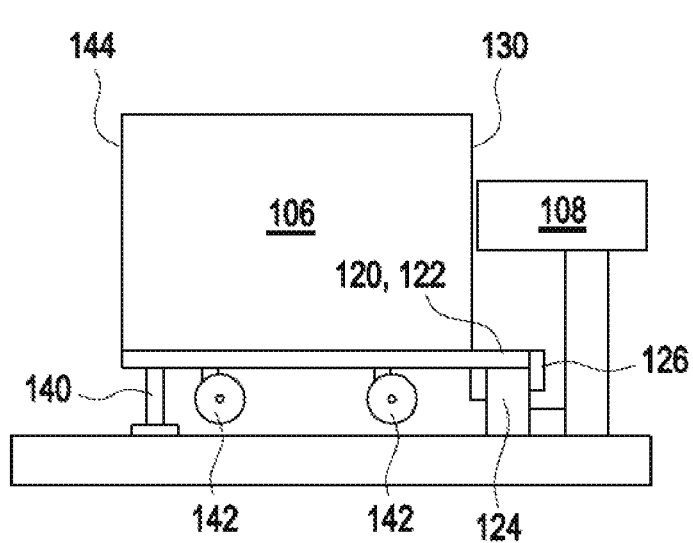

FIGS. 11A to 11H show an operation of coupling the module 106 to a component 106, 108. Particularly, the operation is explained with reference to a coupling to a transport line 108. As shown in FIG. 11A, the coupling process begins with the module 106 being moved on the casters 142 to connection position close to the transport line 108. For example, the module 106 is manually moved. Subsequently, as shown in FIG. 11B, which shows a top view, the module 106 is pushed onto the component protrusion 134 such that the component protrusion 134 is inserted into the infeed 132. Thereby, the module is roughly aligned to the left and right. Subsequently, as shown in FIG. 11C, the module 106 is pushed to the bearing 124 such that it is parallel to the bearing 124 and the engaging member 122 is in contact with the bearing 124. Subsequently, as shown in FIG. 11D, a lifting mechanism (not shown in detail) is used to lift the module 106 at the rear side 130 close the bearing 124 as indicated by arrow 172. Thereby, the casters 142 at the rear side 130 are released from the floor. Subsequently, as shown in FIG. 11E, the module 106 is pushed over the bearing 124 as indicated by arrow 174 such that it is still parallel to the bearing 124 and the engaging member 122 is in contact to the bearing 124. Subsequently, as shown in FIG. 11F, the module 106 is softly lowered with the engaging member 122 onto the bearing 124. Thereby, the engaging member 122 engages the bearing 124 while the casters 142 at the rear side 130 are still spatially separated from the floor. Subsequently, as shown in FIG. 11G, the lifting mechanism is used to lift the module 106 at the front side 144 until it is horizontally oriented as indicated by arrow 176. The horizontal orientation meaning that the edges of the tabletop 110 are at identical vertical positions may be checked by means of a bubble level or the like. Subsequently, as shown in FIG. 11H, the module 106 is fixed in this vertical position by means of the adjustable posts 140 at the front side 144. Further, the lifting mechanism is removed. Optionally, the module 106 may be plugged into connectors (not shown in detail).

The process of coupling as described with reference to FIGS. 11A to 11H represents a rough or coarse alignment of the module 106. Hereinafter, a process of fine alignment of the module 106 or the analytical instrument 104 will be described which may be carried out subsequent or in parallel to the coarse alignment.

As described above, the detector 146 is attached to the module 106 in such a way that all of the component markers 148 and module markers 150 are within the detection range or field of view. FIG. 8 illustrates the detection range or field of view of the detector 146. It covers the surface of the interface area of the transport line 108 and two module markers 150 which area attached to both sides of the module 106 close to the interface area of the transport line 108. The module markers 150 of ArUco type are used to determine the relative position of the module 106, indicated by the module coordinate system 154. The module marker 150 can also be used to identify the module 106. The component marker 148 formed as a point or dot calibration pattern, which is printed on or incorporated into the surface of the interface section of the transport line 108, is used to determine the relative position of the transport line 108, indicated by the component coordinate system 152. In addition, it allows to calculate an image distortion and allows an in situ calibration of the detector 146 since the distances between the points are well defined.

The processor 156 calculates a position deviation of the module 106 from the target position defined by the transport line 108 based on the position data acquired by the image made by the detector 146 and calculates position alignment data based on the position deviation. Particularly, an algorithm is applied by the processor 156 to analyze the image made by the detector 146 and calculate the relative distance and alignment between the component coordinate system 152 of the transport line 108 and the module coordinate system 154 of the module 106. This is converted into a position correction that is input into the alignment device 164 of the module 106 so as to provide a fine alignment of the module 106 and the analytical instrument 104, respectively, relative to the transport line 108.

In summary, the detailed process for determining the position correction for fine alignment and the position correction comprises the following details. The detector 146 such as a camera acquires an image of the module markers 150 such as ArUco landmarks and the component marker 148 such as a point calibration pattern of the interface region of the transport line 108. An algorithm is used for image processing to analyze the module markers 150 to calculate the lateral coordinate system of module 106. The algorithm is used for image processing to analyze the component marker 148. Analyzing the component marker 148 may provide that calibration parameter for camera calibration are extracted, image distortion is calculated and subtracted, and lateral coordinate system of transport line 108 is calculated. Further, a vertical distance deviation of the module 106 from the target position is determined by the distance sensor 166. The algorithm is used to calculate the relative distance between and alignment of the module 106 and the transport line 108 and convert it into a position correction for the analytical instrument 104 of the module 106. The thus calculated results for position correction are transferred into the alignment device 164 to correct the position deviation between the module 106 and the transport line 108. The fine alignment can be supported by the mechanical coarse alignment as described above but does not have to.

Figure 12:
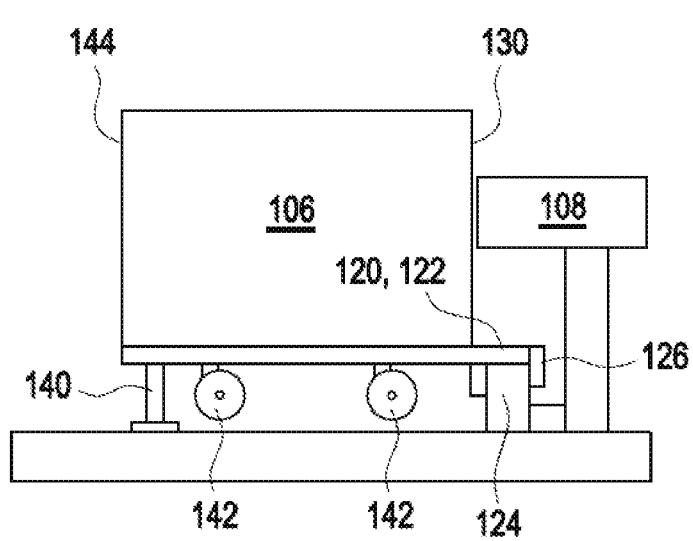
FIGS. 12A to 12G show an operation of decoupling the module from the component.
Figure 12:
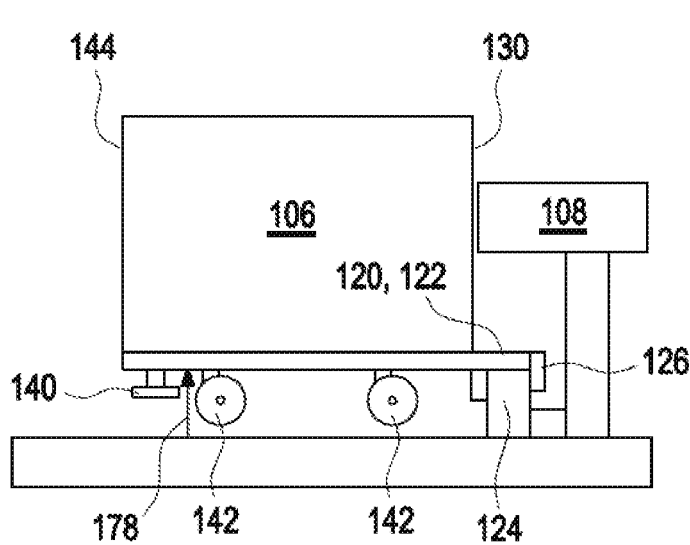
Figure 12:
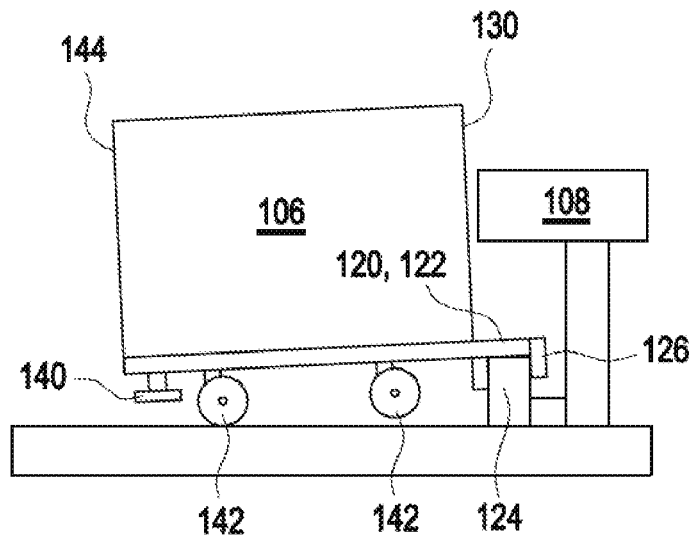
Figure 12:
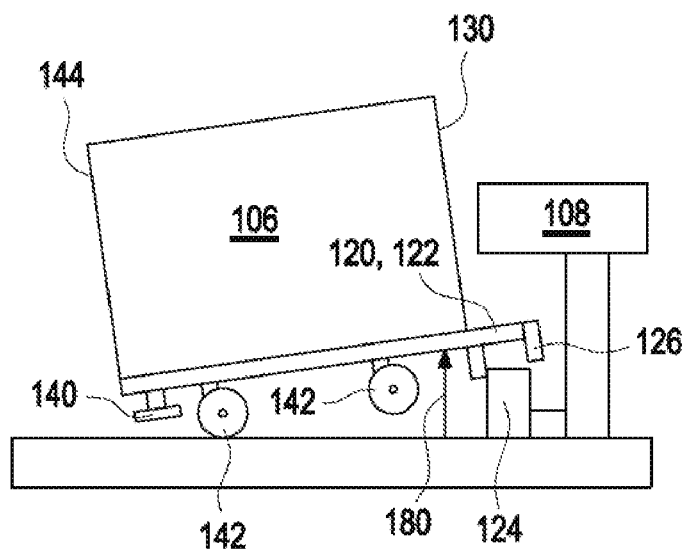
Figure 12:
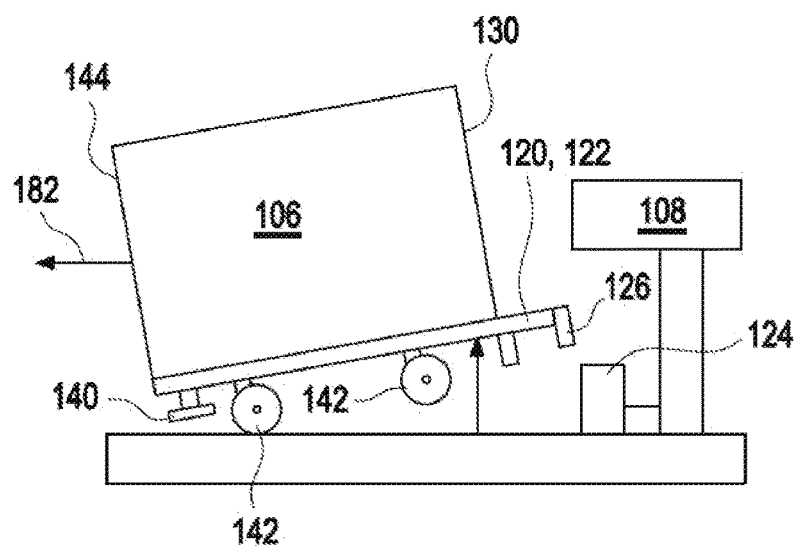
Figure 12:
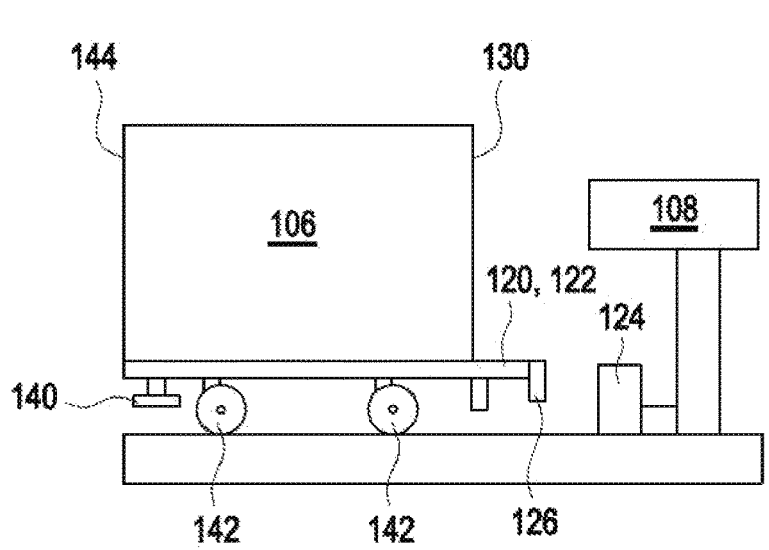
Figure 12:
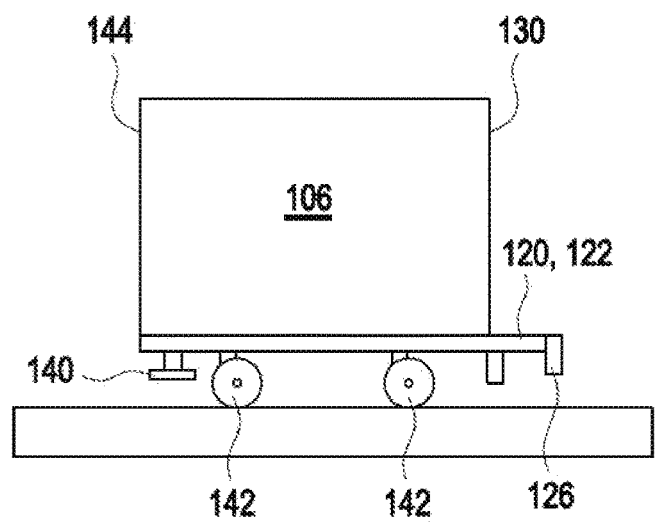

FIGS. 12A to 12G show an operation of decoupling the module 106 from the component 106, 108. Particularly, the operation is explained with reference to a decoupling from a transport line 108. As shown in FIG. 12A, the decoupling process begins with the module 106 being coupled to the transport line 108. The optional connectors are unplugged. Subsequently, as shown in FIG. 12B, the lifting mechanism is used to lift the module 106 at the front side 144. Further, the adjustable posts 140 are turned and lifted into the vertical frame members 116 as indicated by arrow 178.

Subsequently, as shown in FIG. 12C, the module 106 is softly lowered onto the casters 142 at the front side 144. Subsequently, as shown in FIG. 12D, the lifting mechanism is used to lift the module 106 at the rear side 130 close to the bearing 124 as indicated by arrow 180. Subsequently, as shown in FIG. 12E, the module 106 is pulled slightly over the bearing 124 and in front of the bearing 124 as indicated by arrow 182. Subsequently, as shown in FIG. 12F, the module 106 is softly lowered onto the casters 142 at the rear side 130. Further, the module 106 is pulled out of the component protrusion 134 and out of the connection position. Subsequently, as shown in FIG. 12G, the module 106 is moved on the casters 142 to a desired position.

LIST OF REFERENCE NUMBERS

- 100 automated laboratory system
- 102 sample
- 104 analytical instrument
- 106 module
- 108 transport line
- 110 tabletop
- 112 housing
- 114 frame
- 116 vertical frame member
- 118 horizontal frame member
- 120 module connector
- 122 engaging member
- 124 bearing
- 126 hook-shaped protrusion
- 128 lower end
- 130 rear side
- 132 infeed
- 134 component protrusion
- 136 guiding surface
- 138 lateral outer surface
- 140 adjustable post
- 142 caster
- 144 front side
- 146 detector
- 148 component marker
- 150 module marker
- 152 component coordinate system
- 154 module coordinate system
- 156 processor
- 158 reference plane
- 160 transport surface
- 162 handling plane
- 164 alignment device
- 166 distance sensor
- 168 predetermined module plane
- 170 detection range or field of view
- 172 arrow
- 174 arrow
- 176 arrow
- 178 arrow
- 180 arrow
- 182 arrow

What is claimed is:

1. An automated laboratory system comprising:
  a component having a component marker and defining a target position;
  a module having a module connector releasably connected to the component, the module including a module marker;
  a detector mounted on the module, the detector configured to detect the module marker and the component marker and configured to obtain position data of the module indicative of an actual position of the module;
  a processor mounted on the module, the processor programmed to calculate a position deviation of the module from the target position based on the position data and programmed to calculate position alignment data based on the position deviation; and
  an alignment device mounted on the module, the alignment device configured to align the module to the target position based on the position alignment data.

2. The automated laboratory system according to claim 1, wherein the position data includes information on a horizontal position of the module and/or on a vertical position of the module.

3. The automated laboratory system according to claim 1, wherein the detector is a camera.

4. The automated laboratory system module according to claim 1, wherein the component marker and the module marker are located such that the component marker and the module marker are concertedly detectable by the detector.

5. The automated laboratory system according to claim 1, wherein the component marker has a first predetermined dimension and a first predetermined orientation and the module marker has a second predetermined dimension and a second predetermined orientation.

6. The automated laboratory system according to claim 1, wherein the component marker provides a component coordinate system and the module marker provides a module coordinate system, wherein the processor is programmed to calculate the position deviation of the module from the target position based on a relative distance between the component coordinate system and the module coordinate system.

7. The automated laboratory system according to claim 1, wherein the component marker and the module marker allow an in-situ calibration of the detector.

8. The automated laboratory system according to claim 1, further comprising a distance sensor configured to determine a relative vertical position with respect to the component.

9. The automated laboratory system according to claim 8, wherein the distance sensor is configured to determine the relative vertical position based on a distance of reference points at the component from a predetermined module plane.

10. The automated laboratory system according to claim 1, further comprising an analytical instrument, wherein the alignment device is configured to align the analytical instrument to the target position based on the position alignment data.

11. The automated laboratory system according to claim 10, wherein the alignment device is configured to move the analytical instrument within a three dimensional space.

12. The automated laboratory system according to claim 1, wherein the target position is defined by a reference point of or within a reference plane of the component.

13. The automated laboratory system according to claim 1, wherein the component is a transport line of the automated laboratory system or a second module of the automated laboratory system.

14. The automated laboratory system according to claim 13, wherein the target position is defined by a point of a transport surface of the transport line or is defined within the transport surface of the transport line or is defined by a handling plane of the second module.

15. The automated laboratory system according to claim 1, wherein the module connector comprises an engaging member engaging a bearing of the component.

16. The automated laboratory system according to claim 1, wherein the module connector comprises an engaging member engaging a beam or truss of the component.

17. The automated laboratory system according to claim 1, further comprising an infeed receiving a component protrusion of the component or further comprising a module protrusion configured to be inserted into a component infeed of the component.

18. A method of aligning the module of the automated laboratory system according to claim 1, comprising:
- releasably connecting the module to the component of the automated laboratory system;
- detecting the component marker located on the component and obtaining the position data of the module indicative of the actual position of the module using the detector;
- calculating the position deviation of the module from the target position defined by the component based on the position data using the processor;
- calculating the position alignment data based on the position deviation using the processor; and
- aligning the module to the target position based on the position alignment data using the alignment device.

\* \* \* \* \*